US009644074B2

(12) United States Patent
Shipov et al.

(10) Patent No.: US 9,644,074 B2
(45) Date of Patent: May 9, 2017

(54) BENZENE POLYCARBOXYLIC ACID COMPOUNDS AND THEIR USE AS DRUG

(71) Applicant: RDInnovation ApS, Copenhagen (DK)

(72) Inventors: Valery Pavlovich Shipov, St. Petersburg (RU); Evgeny Sergeevich Pigarev, St. Petersburg (RU); Elena I. Fedoros, St. Petersburg (RU)

(73) Assignee: RINNOVATION APS, Copenhagen (DK)

( * ) Notice: Subject to any disclaimer, the term of this patent is extended or adjusted under 35 U.S.C. 154(b) by 0 days.

(21) Appl. No.: 14/389,063

(22) PCT Filed: Apr. 2, 2013

(86) PCT No.: PCT/DK2013/050092
§ 371 (c)(1),
(2) Date: Sep. 29, 2014

(87) PCT Pub. No.: WO2013/143549
PCT Pub. Date: Oct. 3, 2013

(65) Prior Publication Data
US 2016/0017104 A1   Jan. 21, 2016

Related U.S. Application Data

(60) Provisional application No. 61/618,037, filed on Mar. 30, 2012.

(30) Foreign Application Priority Data

Mar. 30, 2012   (DK) .................................. 2012 70159

(51) Int. Cl.
| | | |
|---|---|---|
| C07C 63/00 | (2006.01) | |
| C08H 7/00 | (2011.01) | |
| A61K 47/34 | (2017.01) | |
| C07G 1/00 | (2011.01) | |
| C08H 8/00 | (2010.01) | |
| A61K 8/84 | (2006.01) | |
| A61K 9/48 | (2006.01) | |
| A61K 33/24 | (2006.01) | |
| A61K 45/06 | (2006.01) | |
| A61K 47/48 | (2006.01) | |

(52) U.S. Cl.
CPC ................ C08H 6/00 (2013.01); A61K 8/84 (2013.01); A61K 9/4816 (2013.01); A61K 33/24 (2013.01); A61K 45/06 (2013.01); A61K 47/34 (2013.01); A61K 47/48192 (2013.01); C07G 1/00 (2013.01); C08H 8/00 (2013.01)

(58) Field of Classification Search
CPC ........ A61K 33/24; A61K 45/06; A61K 47/34; A61K 47/48192; A61K 8/84; A61K 9/4816; C07G 1/00; C08H 6/00; C08H 8/00
See application file for complete search history.

(56) References Cited

U.S. PATENT DOCUMENTS

| | | | | |
|---|---|---|---|---|
| 3,910,873 A | * | 10/1975 | Lin | ......................... C08H 6/00 516/47 |
| 4,169,846 A | | 10/1979 | Kidani et al. | |
| 4,657,927 A | | 4/1987 | Cleare et al. | |
| 7,410,655 B2 | | 8/2008 | Shipov et al. | |
| 8,691,194 B2 | * | 4/2014 | Belinky | ................. A61K 8/66 424/62 |
| 2005/0069974 A1 | | 3/2005 | Gladkov et al. | |
| 2010/0075878 A1 | * | 3/2010 | Gizaw | ..................... A61K 8/97 510/119 |
| 2010/0278925 A1 | | 11/2010 | Guerret et al. | |

FOREIGN PATENT DOCUMENTS

| | | |
|---|---|---|
| BY | 6420 | 9/2004 |
| CN | 102174202 A | 9/2011 |
| CN | 102241818 A | 11/2011 |
| DE | 43 18 210 A1 | 12/1994 |
| EP | 0 786 491 A2 | 7/1997 |
| EP | 0298710 | 1/1998 |
| EP | 1 369 122 A1 | 12/2003 |
| EP | 1 864 673 A2 | 12/2007 |
| EP | 1 864 674 A2 | 12/2007 |
| EP | 1864673 | * 12/2007 |
| GB | 2 231 564 | 11/1990 |
| JP | S61087610 A | 5/1986 |

(Continued)

OTHER PUBLICATIONS

Translated 482, 2000.*
Translated 124, 2000.*
A.M. Khvan, et al., "Nitration of Lignin and Sorptive Properties of the Resulting Products," *Chemistry of Natural Compounds*, 38(5):471-472 (2002).
Dalimova G.N., "Modification of Hydrolized Lignin in Acidic and Basic Media," *Chemistry of Natural Compounds*, 42(1): 88-91 (2006).

(Continued)

*Primary Examiner* — Yevegeny Valenrod
*Assistant Examiner* — Blaine G Doletski
(74) *Attorney, Agent, or Firm* — Hamilton, Brook, Smith & Reynolds, P.C.

(57) ABSTRACT

The present invention relates to new benzene polycarboxylic acids compound, which is prepared by alkaline oxidation of hydrolyzed lignin. The present invention also relates to the use of the new benzene polycarboxylic acids compound as part of a composite substance, where the composite substance is prepared by complexing or encapsulating the new benzene polycarboxylic acid compounds with a metal cation. The present invention also relates to a method for preparing the new benzene polycarboxylic acids compound and for its use in cosmetic, nutraceutical and pharmaceutical compositions.

25 Claims, 8 Drawing Sheets

(56) References Cited

FOREIGN PATENT DOCUMENTS

| JP | S63238096 | | 10/1988 |
|----|-----------|---|---------|
| JP | H038788 | | 1/1991 |
| JP | 2009-027957 A | | 2/2009 |
| RU | 2 182 482 C1 | | 9/2000 |
| RU | 2 183 124 C1 | | 9/2000 |
| RU | 2182482 | * | 9/2000 |
| RU | 2183124 | * | 9/2000 |
| RU | 2 350 353 C2 | | 2/2005 |
| RU | 2 368 379 C2 | | 7/2006 |
| WO | WO 01/97750 A2 | | 12/2001 |
| WO | WO 02/24609 A2 | | 3/2002 |
| WO | WO 02/24610 A2 | | 3/2002 |
| WO | WO2008604425 | * | 6/2008 |

OTHER PUBLICATIONS

Notification of Transmittal of the International Search Report and the Written Opinion of the International Searching Authority, or the Declaration in re: International Application No. PCT/DK2013/050092, "Benzene Polycarboxylic Acid Compounds and Their Use as Drug", Date of Mailing Aug. 21, 2013.

Notification of Transmittal of the International Preliminary Report on Patentability in re: International Application No. PCT/DK2013/050092, "Benzene Polycarboxylic Acid Compounds and Their Use as Drug ", Date of Mailing Mar. 21, 2014.

Notice of Rejection for JP Application No. 2015-502098, "Benzene Polycarboxylic Acid Compounds and Their Use as Drug", dated: Aug. 31, 2016.

* cited by examiner $^1H,^1H$-COSY $^1H,^1H$-TOCSY

BENZENE POLYCARBOXYLIC ACID COMPOUNDS AND THEIR USE AS DRUG

This application is the U.S. National Stage of International Application No. PCT/DK2013/050092, filed Apr. 2, 2013, which designates the U.S., published in English, and claims priority under 35 U.S.C. §§119 or 365(c) to Denmark Application No. PA 2012 70159, filed Mar. 30, 2012, and claims the benefit of U.S. Provisional Application No. 61/618,037, filed Mar. 30, 2012.

FIELD OF INVENTION

The present invention relates to new benzene polycarboxylic acid compounds, which are prepared by alkaline oxidation of hydrolyzed lignin. The present invention also relates to the use of the new benzene polycarboxylic acid compounds as part of a composite substance, where the composite substance is prepared by complexing or encapsulating the new benzene polycarboxylic acid compounds with a metal cation. The present invention also relates to a method for preparing the new benzene polycarboxylic acid compound and for its use in cosmetic, nutraceutical and pharmaceutical compositions.

BACKGROUND OF INVENTION

One of the most studied drugs for treatment of cancer is the platinum drug Cisplatin. Cisplatin is a drug with a broad spectrum of activity and is efficient in the therapy of sarcomas, carcinomas and lymphomas to name a few. At the same time, a number of significant disadvantages are associated with this drug. Thus, due to rapid metabolism with formation of inactive protein-bound compounds the drug damages both cancerous and normal cells thereby exhibiting high toxicity, especially nephrotoxicity.

To overcome these problems substantial efforts are put in searching for methods of reduction of toxicity of Cisplatin by means of developing new metalloorganic complexes based on low-molecular organic ligands (U.S. Pat. Nos. 4,169,846; 4,657,927). In this respect, the use of polymeric compounds as chelating or encapsulating agents presents itself as a possible efficient solution of this problem.

US2010/0278925 patent application describes a new type of formulation of organoplatinic compound, comprising at least one organoplatinic compound and at least one associative water-soluble polymer, wherein the said polymer is produced by a polymerization of (Meth)acrylic acid monomers, Urethane monomers and Hemimaleate monomers, and an organoplatinic compound, which is selected from the group of Cisplatin, carboplatin and oxaliplatin. In particular, this invention makes it possible to obtain an oral formulation of the drug in the form of syrup or granulate.

The present invention differs from the above mentioned inventions by using a polymer compound of benzene polycarboxylic acids as a water-soluble polymer to produce organometallic compound preferably for parenteral, enteral and topical application.

Another patent BY6420 describes a polymer-drug formulation of cis-diammineplatinum (II) dichloride exhibiting antitumor effect. Object of the said invention lies in immobilization (encapsulation) of the platinum compound on the surface of 6-carboxycellulose. The resulting drug formulation is used for brain implantation in neurosurgery to prevent recurrence of malignant neoplasms. The said biodegradable polymer-drug formulation of cis-platin exhibits moderate neurotoxicity and improved cytostatic effect.

The present invention differs from the invention disclosed in BY6420 in that the water-soluble polymer of benzene polycarboxylic acids exhibits its own biological effect and that the polymer-drug formulation based on the said polymer can be used for parenteral, enteral and topical application.

In RU 2182482 a process for preparing an anti-cancer agent based on potassium tetrachloroplatinate is disclosed. The said patent discloses a method, in which potassium tetrachloroplatinate reacts with humic compounds. In this method, an aqueous solution of humic substances is treated with a solution of potassium tetrachloroplatinate. The treatment is conducted under irradiation with ultrasonic waves with the power density of 40 W/cm$^2$ and the frequency of 22 kHz for 4 to 8 minutes. The product of the present invention differs from the product described in RU 2182482 by choosing a square-planar coordination compound of platinum (II) as the platinum agent. Moreover, the product of the present invention is produced by using a different method in that the conditions of irradiation are different and that the irradiation power is set per volume of the irradiated product and that the irradiation is performed until the quantity of platinum unreacted with polymer is brought to less than or equal to 25% of the initial quantity and that additionally a thermostating is performed until the quantity of the hydrolysable platinum is brought to less than or equal to 10%. Thereby a different product is obtained. The resulting complex of the present invention is characterized by high stability of bonds and substantially reduced toxicity.

In EP1864673 and RU2368379 another anti-cancer agent is described, which is also produced by reacting coordination compound of platinum (II) with humic compound that is preliminarily subjected to acoustic cavitation caused by exposure to ultrasound with the power density of 0.5 to 5 W/cm$^3$ and the ultrasonic frequency from 18 to 66 kHz. The anti-cancer agent thus obtained is characterized by the content of high-molecular fraction of humic compound of less than or equal to 5%. The product of the present invention differs from the product described in EP1864673 and RU2368379 in that irradiation is carried out until quantity of platinum unreacted with the polymer is brought to less than or equal to 25% of the initial quantity and that additionally a thermostating is performed until the quantity of the hydrolysable platinum is brought to less than or equal to 10%. Thereby a different product is obtained. The resulting complex of the present invention is characterized by high stability of bonds and substantially reduced toxicity.

In RU2183124 a method for producing means protecting an organism against ionizing radiation, namely a substance with radioprotective properties, from materials of natural origin is disclosed. According to this method humic substances are derived from natural raw materials and an aqueous solution of such humic substances is treated with ammonium molybdate. The said treatment with ammonium molybdate is conducted at the temperature of 40±5° C. under irradiation with ultrasonic waves with the power density of 40 W/cm$^2$ and the frequency of 22 kHz for 4 to 8 minutes. The method uses humic substances obtained from oxidized wood lignin. The product of the present invention differs from the invention described in RU2183124 in that the molybdenum salt is selected from a wide range of compounds. Moreover, the product of the present invention is produced by using a different method in that the conditions of irradiation are different and that the irradiation power is set per volume of the irradiated product and that the irradiation is performed until the quantity of molybdenum unreacted with the polymer is brought to less than or equal to 25% of the initial quantity and that additionally a thermostating is performed until the quantity of the hydrolysable molybdenum is brought to less than or equal to 10%. Thereby a different product is obtained. The resulting complex of the present invention is characterized by high stability of bonds and substantially reduced toxicity.

In EP1864674 and RU2350353 another method of producing an agent protecting an organism against ionising radiation is disclosed. This agent is prepared by treating an aqueous solution containing humic substances and ammonium molybdate with wave radiation. The content of ammonium molybdate is selected in the range up to 0.4 parts by weight per 1 part of humic substances, the treatment is conducted until the high molecular fraction of humic substances is brought to the level of less than or equal to 5%. The product of the present invention differs from the invention described in EP1864674 and RU2350353 in that the molybdenum salt is selected from a wide range of compounds. Moreover, the product of the present invention is produced by using a different method in that the conditions of irradiation are different and that the irradiation is performed until the quantity of molybdenum unreacted with the polymer is brought to less than or equal to 25% of the initial quantity and that additionally a thermostating is performed until the quantity of the hydrolysable molybdenum is brought to less than or equal to 10%. Thereby a different product is obtained. The resulting complex of the present invention is characterized by high stability of bonds and substantially reduced toxicity.

Besides the benefits, compositions described in RU2182482, EP1864673, RU2368379, RU2183124, EP1864674 and RU2350353 have a number of disadvantages caused by the fact that organic ligands, which they incorporate, are characterized by variable composition, safety and biological activity and, as a consequence, cannot be used in the development of stable complexes or composite substances suitable for preparation of pharmaceutical, nutraceutical or cosmetic compositions.

The inventors of the present invention have surprisingly found that a novel water-soluble polymer compound of benzene polycarboxylic acids, characterised by low content of mineral and low-molecular impurities and own biological activity can be used for development of stable, safe and potent organometallic complexes.

Improved stability of bonds between the polymer and metal cation in such complexes is achieved through introduction of polymerization, purification and thermostating operations and use of new ultrasonication conditions when the power is set per volume and the treatment is continued until complex is formed with more than 75% of the metallic compound. Thereby a different product is obtained.

The present invention also discloses composite substances based on the new water-soluble polymer compound of benzene polycarboxylic acids, in which the said polymer compound acts as a complexing and/or encapsulating agent forming low-toxicity highly efficient complexes with high-stability bonds. Even in low concentrations these new composite substances show high efficiency. Such composite substances comprising, for example, platinum and molybdenum complexes, demonstrate promising properties. The platinum complexes act as efficient anti-cancer agents and experimental results demonstrate their improved ability to kill cancer cells when compared to the prototypes and such known anticancer agents as Cisplatin and Carboplatin. The molybdenum complexes act as efficient agents for prophylaxis and treatment of diseases caused by cell cycle disruption, which result, for instance, from radiation exposure, cell aging or immune disorders. The pharmaceutical compositions of the present invention can also be used in reducing/minimizing side effects resulting from conventional radiotherapy or chemotherapy.

Chemical properties of the new water-soluble polymer compound of benzene polycarboxylic acids make it possible to obtain a broad range of highly stable complexes, as well as pharmaceutical, nutraceutical and cosmetic compositions for parenteral, enteral and topical administration to human beings and animals.

SUMMARY OF INVENTION

In a first aspect the present invention relates to a novel water-soluble polymer compound of benzene polycarboxylic acids, which is characterized by having an elemental composition of 62-67% C, 3.8-4.2% H, 29-34% O, and less than 0.2% N per dry weight and where the sum of other elements is no more than 1% per dry weight.

In a second aspect the present invention relates to a method for preparing the novel water-soluble polymer compound of benzene polycarboxylic acids, in which a lignin-containing starting raw material is subjected to alkaline treatment, followed by acid density gradient treatment in order to obtain a crude water-soluble polymer compound of benzene polycarboxylic acids, and finally subjecting the crude compound to purification.

In a third aspect the present invention relates to the novel water-soluble polymer compound for use in prophylaxis, treatment and modification of human and animal diseases and to pharmaceutical compositions comprising the novel water-soluble polymer compound for use in prophylaxis, treatment and modification of human and animal diseases.

In a forth aspect the present invention relates to a cosmetic composition or a nutraceutical composition comprising the novel water-soluble polymer compound.

In a fifth aspect the present invention relates to a composite substance comprising the novel water-soluble polymer compound of benzene polycarboxylic acids and a metal cation and optionally an anticancer agent and its use in a pharmaceutical composition for prophylaxis, treatment or modification of a human or an animal disease.

In a sixth aspect the present invention relates to a process for preparing the composite substance comprising the novel water-soluble polymer compound of benzene polycarboxylic acids and a platinum (II) square planar coordination compound.

In a seventh aspect the present invention relates to the composite substance comprising the novel water-soluble polymer compound of benzene polycarboxylic acids and a platinum (II) square planar coordination compound for use as a drug or for use in the preparation of a pharmaceutical composition.

In an eighth aspect the present invention relates to the use of the drug or pharmaceutical composition comprising the composite substance comprising the novel water-soluble polymer compound of benzene polycarboxylic acids and a platinum (II) square planar coordination compound in the prophylaxis, treatment or palliative care or for modifying a disease of a mammal, such as for example cancer.

In a ninth aspect the present invention relates to a composite substance comprising the novel water-soluble polymer compound of benzene polycarboxylic acids and a molybdenum compound, wherein the polymer compound of benzene polycarboxylic acids encapsulates or forms a complex with the said molybdenum compound.

In a tenth aspect the present invention relates to a process for preparing the composite substance comprising the novel water-soluble polymer compound of benzene polycarboxylic acids and a molybdenum compound.

In an eleventh aspect the present invention relates to the composite substance comprising the novel water-soluble polymer compound of benzene polycarboxylic acids and a molybdenum compound for use as a drug or for use in the preparation of a pharmaceutical composition.

In a twelfth aspect the present invention relates to the use of the drug or pharmaceutical composition comprising the composite substance comprising the novel water-soluble polymer compound of benzene polycarboxylic acids and a molybdenum compound in the prophylaxis, treatment or palliative care of a mammal suffering of a disease such as for example a cell cycle disruption disease or for modifying the said disease.

In a thirteenth aspect the present invention relates to pharmaceutical compositions for use in reducing/minimizing side effects resulting from conventional radiotherapy or chemotherapy.

DETAILED DESCRIPTION OF THE INVENTION

Figure 1:
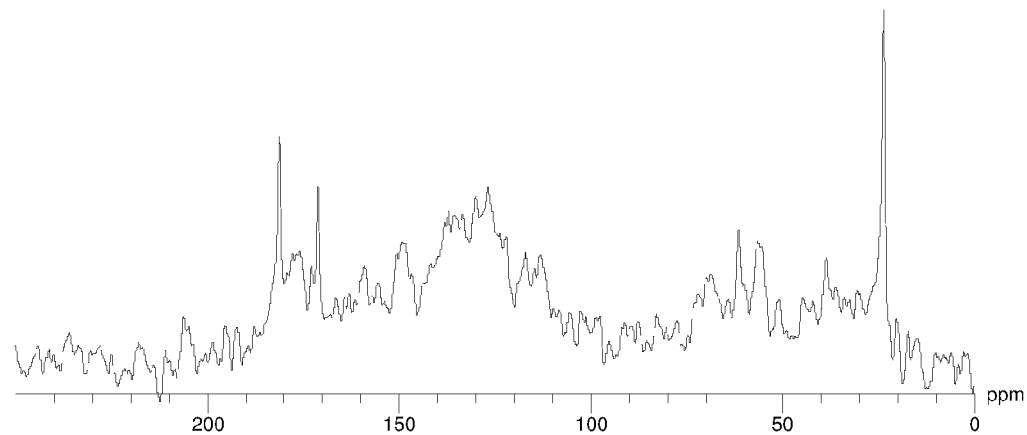
FIG. 1. $^{13}$C NMR spectrum of humic acids according to prototype RU2182482.

The present invention relates to a novel water-soluble polymer compound of benzene polycarboxylic acids, which is characterized by the following elemental composition: 62-67% C, 3.8-4.2% H and 29-34% O, less than 0.2% N per dry weight and sum of other elements (inorganic impurities) is below 1% per dry weight. This novel compound possesses its own pharmacological activity, an enhanced degree of purity as well as an improved ability to form stable complexes or encapsulate various agents.

By the term "water-soluble polymer compound of benzene polycarboxylic acids" as used herein is meant a polymer, primarily comprising water-soluble polybasic aromatic carbonic acids.

The novel water-soluble polymer may be further characterized using the $^{13}$C NMR, IR and FTICR-MS methods.

According to $^{13}$C NMR, the amount of carbon of $CH_n$ aliphatic groups detected in the 0-48 ppm range constitutes 15-22%; amount of aromatic carbon $C_{AR}$ detected in the 108-145 ppm range constitutes 30-42%; amount of carbon of carboxylic and ester COO groups detected in the 165-187 ppm range constitutes 5-13% and amount of carbon of ketonic groups C=O detected in the 187-220 ppm range constitutes 2-8%. Total amount of low-molecular impurities detected at 168.5 ppm (carbonate-anion), 171 ppm (formate-anion), 173 ppm (oxalate-anion) and 181-182 ppm (acetate-anion) is below 1 percent.

By the term "low-molecular impurity" as used herein is meant a compound with molecular weight below 300 Da, which was not polymerized.

Noticeable specific stretching vibrations of ionized asymmetric COO-groups with peaks at 1410 cm$^{-1}$ can be seen on IR-spectra of the polymer. Wide complex absorption band corresponding to the mixture of aliphatic and aromatic carbonic acids is seen in the 1500-1700 cm$^{-1}$ range. Along with carboxylic acids the polymer also contains a significant amount of phenolic compounds bound to each other with hydrogen bonds. This is demonstrated by the presence of absorption bands in the following regions: 3400-3600 cm$^{-1}$ (OH), 1050 cm$^{-1}$ (C—O), 1250-1300 cm$^{-1}$ (OH). 2800-3000 cm$^{-1}$ region contains absorption band with peaks at 2928 cm$^{-1}$ and 2853 cm$^{-1}$ corresponding to valent vibrations of CH-groups in $CH_3$ and $CH_2$ groups. More or less expressed absorption peaks identified at 1750 cm$^{-1}$ correspond to vibrations of C=O groups.

A 1500 Da fragment of the novel polymer compound of the present invention can be represented by the following brutto formula: $(C_3H_2O)_{x1}(C_2H_2O)_{x2}(CH_2)_{x3}$, where $x_1 \leq 12$, $x_2 \leq 9$, $x_3 \leq 33$.

Benzene polycarboxylic acids (aromatic components, predominantly defined as methyl esters of benzene polycarboxylic acids) are the main monomers of the polymer. Additionally, the polymer of benzene polycarboxylic acids comprises monomers, such as saturated aliphatic carboxylic acids, saturated aliphatic hydroxycarboxylic acids, monounsaturated aliphatic carboxylic acids, monounsaturated aliphatic hydroxycarboxylic acids and polyunsaturated aliphatic carboxylic acids.

Saturated aliphatic carboxylic acids correspond to the general formula—$C_nH_{2n}O_2$, where n is from 12 to 26. Saturated aliphatic hydroxycarboxylic acids correspond to the general formula—$C_nH_{2n}O_3$, where n is from 16 to 26. Monounsaturated aliphatic carboxylic and hydroxycarboxylic acids correspond to the following formulas—$C_nH_{2n-2}O_2$, $C_nH_{2n-2}O_3$, $C_nH_{2n-2}O_4$, $C_nH_{2n-2}O_5$, where n is from 14 to 28. The above-described compounds are responsible for surface-active properties of the polymer.

Polyunsaturated aliphatic carboxylic acids are represented by 13-cis-retinoic acid, 6Z, 9Z,12Z,15Z-octadecatetraenoic acid, cis,cis,cis-6,9,12-octadecatrienoic acid, (9R,13R)-2-oxo-5-pentyl-3-cyclopentene-1-octanoic acid, 9S-hydroperoxy-10E,12Z,15Z-octadecatrienoic acid, C13(S)-hydroxyoctadeca-9Z,11E-dienoic acid, 10S,11S-epoxy-9S-hydroxy-12Z-octadecenoic acid, 9S,12S,13S-trihydroxy-10E,15Z-octadecadienoic acid, 5,6-dehydroarachidonic acid and 15(S)-hydroxy-(5Z,8Z,11Z,13E,17Z)-eicosapentaenoic acid. Antitumor and antioxidant effects of many compounds that belong to this last series (for instance, 13-cis-Retinoic (Isotretinoin), C13(S)-Hydroxyoctadeca-9Z,11E-dienoic acid, 5,6-Dehydroarachidonic acid) are also retained in the polymer of this invention.

The main group of monomers (aromatic components) comprises the following monomers: 3-benzyloxy-4,5-dihydroxy-benzoic acid methyl ester, 5-(furan-2-carbonyloxy)-2-methyl-benzofuran-3-carboxylic acid methyl ester, 2,6-dimethyl-benzo(1,2-b,4,5-b')difuran-3,7-dicarboxylic acid dimethyl ester, 5-(furan-2-carbonyloxy)-2-methyl-benzofuran-3-carboxylic acid ethyl ester, rhamnetin, methyl ((4-methyl-6-oxo-6h-benzo(c)chromen-3-yl)oxy)acetate hydrate, bis(2-(methoxycarbonyl)phenyl) carbonate, sulochrin, 2,6-diacetyl-7,9-dihydroxy-8,9b-dimethyldibenzofuran-1,3(2H,9bH)-dione, O-acetylsalicylic anhydride, 4-ho-3-((6-ho-benzo(1,3)dioxol-5-yl)-(3-methoxy-phenyl)-methyl)-5h-furan-2-one, 2,3-bis-benzoyloxy-succinic acid, methyl 5-hydroxy-7,8-dimethoxy-1,3-dioxo-1,3,10,11-tetrahydrobenzo[5,6]cycloocta[1,2-c]furan-4-carboxylate, (1-methoxycarbonylmethoxy-6-oxo-6h-benzo(c)chromen-3-yloxy)-acetic acid methyl ester, atranorin and phenylpropanoid-substituted epicatechins. Many compounds that belong to this group exhibit antibiotic and antitumor effects.

The present invention is also directed to a method for preparing the water-soluble polymer compound of benzene polycarboxylic acids. The novel polymer compound of the present invention may be prepared according to the method set forth below.

In the first step of the method a lignin-containing material is provided as a starting raw material. Examples of such lignin-containing materials include oxidized lignin, wood, peat, plant remnants, leftovers of pulp factories. The most preferred lignin-containing starting raw material is produced from conifer trees and is characterized by having a pH from 5.5 to 7, moisture content from 50 to 70% and comprising no more than 32% of polysaccharides, no less than 66% of lignin and no more than 2% of water-soluble compounds.

In the second step of the method a water suspension of lignin-containing raw material is subjected to treatment with alkali at a pH of 13±0.5 and a pressure of 2.2±0.3 MPa. Examples of alkalis that can be used include hydroxides of alkaline and/or alkaline-earth metals and/or ammonia. The preferred alkali, however, is sodium hydroxide. By this alkaline treatment a solution of sodium salts of benzene polycarboxylic acids is obtained as a result of the hydrolysis and oxidation.

In the third step of the method, the solution of sodium salts of benzene polycarboxylic acids is subjected to acid density gradient treatment. In this step, the solution of sodium salts of benzene polycarboxylic acids is treated with mineral acid and subjected to treatment with centrifugal forces. As a result, a density gradient is created and condensation and polymerization of benzene polycarboxylic acids takes place. Examples of mineral acids that can be used include such soluble stable acids as sulphuric, orthophosphoric, nitric and hydrochloric. The preferred mineral acid, however, is hydrochloric acid.

The forth step is a purification step, where purification with one or more purifying processes such as extraction, flotation, distillation, filtration, precipitation, centrifugation, decantation and/or dialysis is performed to remove low-molecular impurities. The purification is continued until the quantity of low-molecular impurities detected with $^{13}C$ NMR or another representative method (for example, gas chromatography) falls below 1% of dry weight of the polymer.

The best mode of the method of manufacturing of the polymer is disclosed in Example 1. Results of comparison of the polymer of this invention with the humic acids obtained in accordance with RU2182482 are also described in Example 1.

The present invention is also directed to composite substances that comprise the novel water-soluble polymer compound of benzene polycarboxylic acids and a metal cation and optionally an anticancer agent. In preferred composite substances the water-soluble polymer compound of benzene polycarboxylic acids acts as a complexing and/or an encapsulating agent.

By the term "water-soluble polymer" as used herein is meant a polymer, which is soluble in water at neutral or alkaline pH at the concentration of 5 wt %.

By the term "complexing agent" as used herein is meant an electron-donor compound, which is able to form soluble complexes with metal ions, where these complexes may be coordination and/or chelate complexes. In these complexes fragments of the polymer of the present invention are the ligands of the central metal ion. The metal ion may be a 2s-5s or 3d-5d metal. Examples of such 2s-5s or 3d-5d metals are platinum, molybdenum, lithium, calcium, potassium, magnesium, manganese, iron, zinc, silver, palladium and copper.

By the term "encapsulating agent" as used herein is meant a large molecule, which is able to confine small molecules and shield them from impact of the surrounding environment. Encapsulating agent in contrast to complexing agent does not form stable chemical bonds with the small molecules that it confines. Therefore, by the term "encapsulating" is meant "the process of confinement of small molecules within a larger molecule".

Additionally, inventors of the present invention have undertaken a task to prepare pharmaceutical, nutraceutical and cosmetic compositions comprising such a novel water-soluble polymer and optionally one or more further excipients.

The cosmetic compositions are made up of the novel water-soluble polymer compound together with other ingredients that are typically present in such cosmetic compositions. The cosmetic compositions may further comprise other compounds possessing, for instance, bactericide, wound healing, antioxidant properties. Thus to obtain a bactericide composition, silver cation is used as a metal exhibiting bactericide activity. To obtain a wound healing composition, copper is used as a metal exhibiting wound healing activity. To obtain an antioxidant composition, lithium is used as a metal, organic-mineral complexes of which exhibit antioxidant activity. The cosmetic compositions can be used for skin correction or for curing the same.

The nutraceutical compositions are made up of the novel water-soluble polymer compound together with other ingredients that are typically present in such nutraceutical compositions. The nutraceutical compositions may further comprise nutrients. As nutrients (dietary minerals vital for a living organism), such macro-elements as, for instance, iron, potassium, calcium, magnesium and other and/or such micro-elements as, for instance, lithium, silver, zinc, copper, manganese, palladium and other can be used. The nutraceutical compositions can be used for restoration of nutritional balance.

The pharmaceutical compositions comprise in some embodiments the novel water-soluble polymer compound, whereas in other embodiments the pharmaceutical compositions comprise a composite substance comprising the novel water-soluble polymer compound and a metal cation. The pharmaceutical compositions may additionally comprise an anticancer agent, which may be selected from the Group L of the World Health Organization Anatomical Therapeutic Chemical (ATC) classification system. Good examples of such anticancer agents are Cyclophosphamide, Cisplatin, Methotrexate, Fluorouracil, Doxorubicin, Goserelin, Tamoxifen, Filgrastim, interferon-alpha, interleukin. The pharmaceutical composition can be used for therapy, prophylaxis or modification of diseases. Examples of excipients that can be used in pharmaceutical compositions according to the present invention include compounds selected from the group consisting of antiadherents, binders, coating agents, disintegrants, fillers, solvents/co-solvents, flavours, colours, lubricants, glidants, preservatives, sorbents, sweeteners, carriers, polymers for modified release of API, polymers for protection of API, buffering agents, antioxidants, wetting agents, antifoaming agents, thickening agents, humectants or mixtures thereof.

Pharmaceutical compositions according to the present invention are preferably formulated so as to be administered by the oral, mucosal or linguistic route. Hence, the pharmaceutical compositions of the invention are preferably formulated as tablets, lozenges, chewing gums, liquid viscous pastes, firm candies or lollipops or as chewable candies or gelled drops.

Some embodiments of the present invention are directed to a composite substance, which comprises the novel water-soluble polymer compound and a metal cation. Among the types of composite substances mentioned above, strongest interest is drawn by composite substances containing the polymer and a platinum compound or those containing the polymer and a molybdenum compound.

It is known that bivalent platinum complexes, which distinguish themselves in having a square-planar structure, that is such a structure where the platinum ion occupies central position and ligands are placed on the sides of the square laying in the same plane, are the most potent antitumour compounds. In such compositions, valence angle of the platinum coordination ion exactly matches the distance between neighbouring guanine molecules of the DNA, which allows it to inhibit synthesis of the latter through formation of intrastrand adducts. In a preferred embodiment of the present invention cis-diammineplatinum(II) dichloride, potassium tetrachloroplatinate or mixtures thereof are used as the bivalent platinum complexes for synthesis of a composite substance.

The present invention is also directed to a process of preparing the composite substance according to the present invention. According to the invention, such a composite substance comprising the polymer compound of the present invention and a platinum (II) square-planar coordination compound may be obtained by exposing the substance to wave radiation and more particularly to ultrasound treatment with a power density in the range of 0.5-5 W/cm$^3$ and a frequency in the range of 18-66 kHz for 1 to 30 minutes until the content of unbound platinum (i.e. platinum, which has not reacted with the polymer) falls below 25% of its original quantity.

In the next step the composite substance is undergoing thermostating (i.e. storage under specific temperature conditions) for 1 to 30 days at 2° C. to 40° C. until the portion of unbound platinum falls below 10% of its original quantity and formation of complex between platinum (II) square-planar coordination compound and the polymer is accomplished.

In a final step, the composite substance undergoes purification in order to obtain a product suitable for pharmaceutical application. Purification may comprise one or more purifying processes such as sterilizing filtration, autoclaving or irradiation.

In the composite substance, platinum is encapsulated or forms complex with one of the following structures of the polymer of benzene polycarboxylic acids:

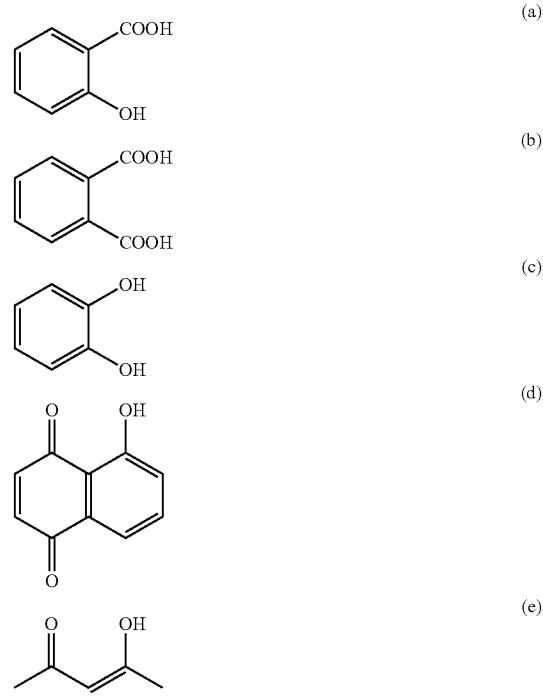

where the structures a, b, c and d represent moieties of the aromatic components and structure e represents a moiety of the aliphatic components mentioned above.

Presence of these structures is demonstrated by characteristic IR absorption bands at 3400-3600 cm$^{-1}$, 2800-3000 cm$^{-1}$, 1500-1700 cm$^{-1}$, 1410 cm$^{-1}$, 1250-1300 cm$^{-1}$ and 1050 cm$^{-1}$. Whereas, intensity of the peaks at 3400-3600 cm$^{-1}$, 1500-1700 cm$^{-1}$, 1410 cm$^{-1}$ and 1250-1300 cm$^{-1}$ is smaller than that of the polymer compound of the benzene polycarboxylic acids due to bond formation between the polymer and platinum.

Empirical formula of the platinum-containing composite substance was established using the $^{13}$C NMR (brutto formula) and 2D NMR methods, according to which it is composed of individual repeated fragments of the polymer: ($C_3H_2O$), ($C_2H_2O$), ($CH_2$). Due to the fact that in solutions the polymer compound exists only in the form of colloidal micelles it is difficult to establish its true molecular mass. Precise molecular formula of the polymer has not been established yet and thus more specific coefficients cannot be instantiated in its brutto formula. According to the present invention composition of the platinum-containing composite substance is represented by the following general formula:

$$(C_3H_2O)_{x1}(C_2H_2O)_{x2}(CH_2)_{x3}(Pt(NH_3)_2)_{x4}.$$

At that, the following stoichiometric ratios are respected at $x_4=1$, $x_1 \leq 12$, $x_2 \leq 9$ and $x_3 \leq 33$. This brutto formula describes 1500-2000 Da fragment of the composite substance. When a composite substance of a larger or a smaller molecular weight is obtained, the $x_1$, $x_2$, $x_3$ and $x_4$ coefficients are changed proportionally. At that, they remain natural positive full or fractional numbers.

The best mode for preparing the composite substance comprising the polymer compound and a platinum compound is described in Example 2.

The present invention also relates to a drug comprising the polymer compound and a platinum (II) compound.

The present invention also relates to a pharmaceutical composition comprising the drug of polymer compound and platinum (II) compound. This pharmaceutical composition may optionally comprise one or more further excipients. Preferably, the one or more further excipients are selected from the group consisting of antiadherents, binders, coating agents, disintegrants, fillers, solvents/co-solvents, flavours, colours, lubricants, glidants, preservatives, sorbents, sweeteners, carriers, polymers for modified release of API, polymers for protection of API, buffering agents, antioxidants, wetting agents, antifoaming agents, thickening agents, humectants and mixtures thereof.

The drug and the pharmaceutical composition comprising the drug can be used in the treatment of a disease such as in the treatment of various types of cancer including metastatic breast cancer. Examples of cancers that can be treated by the pharmaceutical compositions of the present invention include, but are not limited to, breast cancer, pancreatic cancer, urinary bladder cancer, prostate cancer, colon cancer and head and neck cancer. The drug and pharmaceutical composition may also be used in prophylaxis or palliative care of a mammal suffering of cancer or for modifying the said cancer. By the term "modifying the said cancer" as used herein is meant the situation where the drug does not ensure direct anticancer effect, but affects development of the disease and/or changes quality of life of the cancer patient. The drug may be administered by any usual route of administration, but preferably the administration route is parenteral, enteral or topical and in case of parenteral administration, intramuscular injections are preferred. The mammals to be treated are in one embodiment non-food producing species. Preferably the said non-food producing species may be selected among human beings, dogs, cats and horses.

When used in the treatment of cancer, pharmaceutical compositions based on the composite substance ensure significant inhibition of tumour growth in preclinical trials and clinical trials in human beings (Example 3).

Inventors of the present invention also obtained a range of composite substances based on the water-soluble polymer compound of benzene polycarboxylic acids and a molybdenum compound. Preferably, the molybdenum compound was selected among such molybdenum acid salts as ammonium molybdate, ammonium molybdate tetrahydrate, potassium molybdate, sodium molybdate, sodium molybdate dihydrate and mixtures thereof.

In the composite substance, molybdenum is encapsulated or forms complex with one of the following structures of the polymer of benzene polycarboxylic acids:

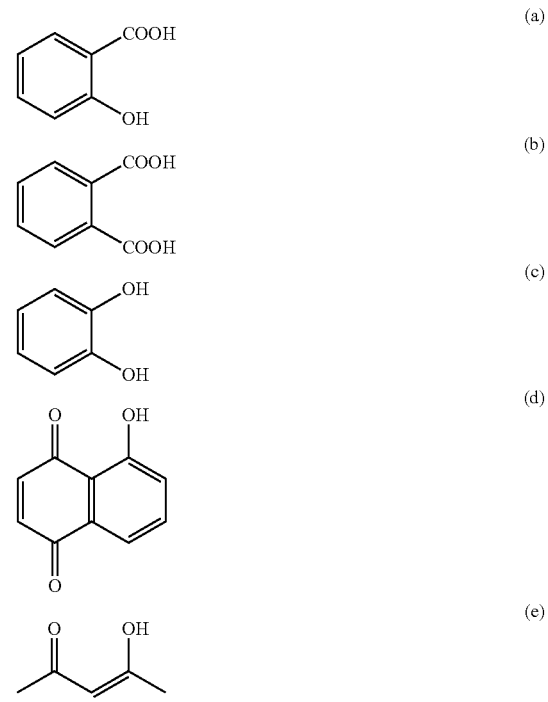

where the structures a, b, c and d represent moieties of the aromatic components and structure e represents a moiety of the aliphatic components mentioned above.

Presence of these structures is demonstrated by characteristic IR absorption bands at 3400-3600 cm$^{-1}$, 2800-3000 cm$^{-1}$, 1500-1700 cm$^{-1}$, 1410 cm$^{-1}$, 1250-1300 cm$^{-1}$ and 1050 cm$^{-1}$. At that intensity of the peaks at 3400-3600 cm$^{-1}$, 1500-1700 cm$^{-1}$, 1410 cm$^{-1}$ and 1250-1300 cm$^{-1}$ is smaller than that of the polymer compound of the benzene polycarboxylic acids due to bond formation between the polymer and molybdenum.

According to the present invention, composition of the molybdenum-containing composite substance can be represented by the following general formula:

$$(C_3H_2O)_{x1}(C_2H_2O)_{x2}(CH_2)_{x3}(MoO_3)_{x4}(H_2O)_{x5}(NH_4)_{x6}.$$

At that, the following stoichiometric ratios are respected: at $x_4=1.5$, $x_1 \leq 12$, $x_2 \leq 9$ and $x_3 \leq 33$, $x_5 \leq 2$ and $x_6 \leq 2$. This brutto formula describes 1500-2000 Da fragment of the composite substance. When a composite substance of a larger or a smaller molecular weight is obtained, the $x_1$, $x_2$, $x_3$, $x_4$, $x_5$ and $x_6$ coefficients are changed proportionally. At that, they remain natural positive full or fractional numbers.

The present invention is also directed to a process of preparing the composite substance according to the present invention. According to the invention, such a composite substance comprising the polymer compound of the present invention and a molybdenum compound may be obtained by exposing the substance to wave radiation and more particularly to ultrasound treatment with a power density in the range of 0.5-5 W/cm$^3$ and a frequency in the range of 18-66 kHz for 1 to 30 minutes until the content of unbound molybdenum (molybdenum, which has not reacted with the polymer) falls below 25% of its original quantity.

In the next step the composite substance is undergoing thermostating (i.e. storage under specific temperature conditions) for 1 to 30 days at 2° C. to 40° C. until the portion of unbound molybdenum falls below 10% of its original quantity and formation of complex between molybdenum compound and the polymer is accomplished.

In the final step, the composite substance undergoes purification in order to obtain a product suitable for pharmaceutical application. Purification may comprise one or more purifying processes such as sterilizing filtration, autoclaving or irradiation.

The best mode of preparing the composite substance comprising the polymer and a molybdenum compound is described in Example 4.

The present invention also relates to a drug comprising the polymer compound and a molybdenum compound.

The present invention also relates to a pharmaceutical composition comprising the drug of polymer compound and molybdenum compound. This pharmaceutical composition may optionally comprise one or more further excipients. Preferably, the one or more further excipients is selected from the group consisting of antiadherents, binders, coating agents, disintegrants, fillers, solvents/co-solvents, flavours, colours, lubricants, glidants, preservatives, sorbents, sweeteners, carriers, polymers for modified release of API, polymers for protection of API, buffering agents, antioxidants, wetting agents, antifoaming agents, thickening agents and humectants.

The drug and the pharmaceutical composition comprising the drug can be used in the treatment of a mammal suffering of a cell cycle disruption disease such as for example, carcinogenesis induced by radiation or caused by natural ageing of cells. The drug and pharmaceutical composition may also be used in palliative care of a mammal suffering of a cell cycle disruption disease such as for example, carcinogenesis induced by radiation or caused by natural ageing of cells or for modifying the said disease. By the term "modifying the said disease" as used herein is meant the situation where the drug does not ensure direct cure, but affects development of the disease and/or changes quality of life of the patient. The drug may be administered by the oral route. The mammals to be treated are in one embodiment non-food producing species. Preferably the said non-food producing species may be selected among human beings, dogs, cats and horses.

Example 5 discloses results of the studies of a pharmaceutical composition comprising the polymer compound and the molybdenum compound, where the said pharmaceutical composition is used to induce cell response.

EXAMPLES

The invention is further illustrated with reference to the following examples, which are not intended to be in any way limiting the scope of the present invention.

Comparative Example 1A

Method of Producing Humic Acids as Disclosed in RU2182482 and Characterisation of the Said Compound For comparison purpose known humic acids according to example 1 of the Russian patent RU 2182482 were prepared and characterized as described below.
Preparation Hydrolysed lignin—non-specific enteral sorbent (available under the trade-name of "Polyphepanum", Scientek Ltd) was used as starting material.

A solution of 1 kg of starting material, 100 g of sodium hydroxide and 8.1 kg of water was treated for one hour in oxidation reactor equipped with mechanical stirring mechanism at a temperature of 160° C., a pressure of 2.5 MPa and with supply of oxygen in an amount of 5 l/min. The reaction mixture was then cooled to room temperature and the solid residue was removed by filtration. pH of the filtrate, an alkaline solution containing humic substances, was adjusted to 2-3 using sulphuric acid. Residues of the humic acids were isolated using filtration and sequentially rinsed with distilled water and a water-alcohol mixture until a pH of 6.0-6.5 was obtained. The resulting product was then dried at a temperature of 105° C. until a homogenous mass was obtained.
Characterisation The humic acids prepared as described above were characterized as follows.

Ash (mineral impurities): 13.5%

Elementary composition: C 67.0%, H 4.0%, N 1.0%, O 0.28%

Low molecular impurities: identified by the following $^{13}C$ NMR peaks: 168.5 ppm (carbonate-anion), 171 (formate-anion), 173 (oxalate-anion), 181-182 ppm (acetate-anion). Total amount of identified impurities constituted 4.1% of dry weight.

The structure of the humic acids was analysed using $^{13}C$ NMR. The result is presented in Table 1 below and in FIG. 1.

TABLE 1

| Result of $^{13}C$ NMR analysis INTEGRAL INTENSITIES, % ± STANDARD DEVIATIONS | | | |
|---|---|---|---|
| 0-48 | 108-145 | 165-187 | 187-200 |
| 18.0 ± 2.5 | 29.0 ± .2.1 | 13.0 ± 0.3 | 8.0 ± 3 |

Example 1B

Method of Producing the Water-Soluble Polymer Compound of Benzene Polycarboxylic Acids of the Present Invention and Characterisation of the Said Compound Preparation Hydrolysed lignin—non-specific enteral sorbent (available under the trade-name of "Polyphepanum", Scientek Ltd) was used as starting material.

This starting material has the following physical-chemical characteristic: pH of 6.5, moisture content of 66.63%, content of polysaccharides equals 25%, content of lignin equals 72.5%, water-soluble compounds equal 1.5% per dry weight.

Step a: 0.998 kg of Polyphephanum was placed in a 15-liter vessel and 6 kg of distilled water were added. The mixture was stirred thoroughly.

Step b: Approximately 2 liters of a 50% sodium hydroxide solution were intermittently added to the mixture of step a to obtain pH 13. The suspension was then subjected to alkaline treatment in a 10 liters oxidative-hydrolytic destruction reactor. When the temperature and pressure reached 160° C. and 2.2 MPa, respectively, the air supply was reduced to 5 dm³/min and treatment continued for 2 more hours to ensure complete hydrolysis and oxidation of the insoluble lignin.

The resulting product, a solution of sodium salts of benzene polycarboxylic acids, was then isolated from the solid residue using press-filter.

Step c: The solution of sodium salts of benzene polycarboxylic acids obtained in step b was then treated with hydrochloric acid until a pH of 1-2 was obtained and then subjected to the effect of centrifugal forces for 15 minutes at 2500 rpm to induce polymerization of benzene polycarboxylic acids through the density gradient. Densified crude polymer of benzene polycarboxylic acids was thus obtained.

Step d: The crude polymer of benzene polycarboxylic acids was then placed in 3.5 kDa dialysis tubes and dialyzed against distilled water until the quantity of low-molecular impurities, detected with $^{13}C$ NMR or another representative method (for instance, gas chromatography), reached 1% of dry weight of the polymer. The final purified polymer compound of benzene polycarboxylic acids was obtained.

The final purified polymer compound of benzene polycarboxylic acids was then dried for further characterization.

Characterization

The polymer obtained in step d was characterized as follows.

Description: black crystals.

Figure 2:
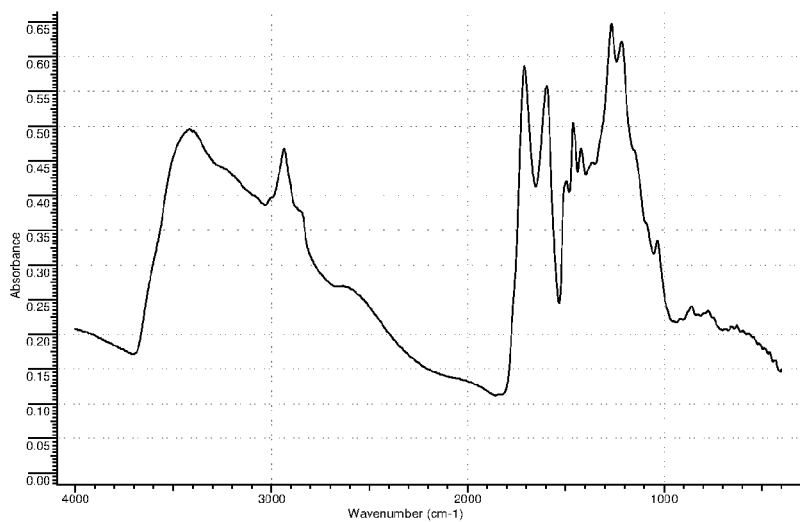
FIG. 2. IR spectrum of the polymer compound of benzene polycarboxylic acids of the present invention.

Identity: IR spectrum absorption bands at: 3400-3600 cm$^{-1}$ (OH), 1050 cm$^{-1}$ (C—O), 1250-1300 cm$^{-1}$ (OH). 2800-3000 cm$^{-1}$ region contains absorption band with peaks at 2928 and 2853 cm$^{-1}$, corresponding to valent vibrations of CH-groups in CH$_3$ and CH$_2$. More or less expressed absorption peak was identified at 1750 cm$^{-1}$, corresponding to vibrations of C=O groups. IR-spectrum of the polymer is presented on FIG. 2.

Solid residue: 93.25%

Ash (mineral impurities): 0.67%

Chlorides: below 0.03%

Heavy metals: below 0.001%

Elementary composition: C 62.5%, H 3.8%, N 0.18%, O 33.7%

Low molecular impurities: were identified with the following peaks of $^{13}C$ NMR spectrum: 168.5 ppm (carbonate-anion), 171 (formate-anion), 173 (oxalate-anion), 181-182 ppm (acetate-anion). Total amount of identified impurities constituted 0.8% per dry weight.

Figure 3:
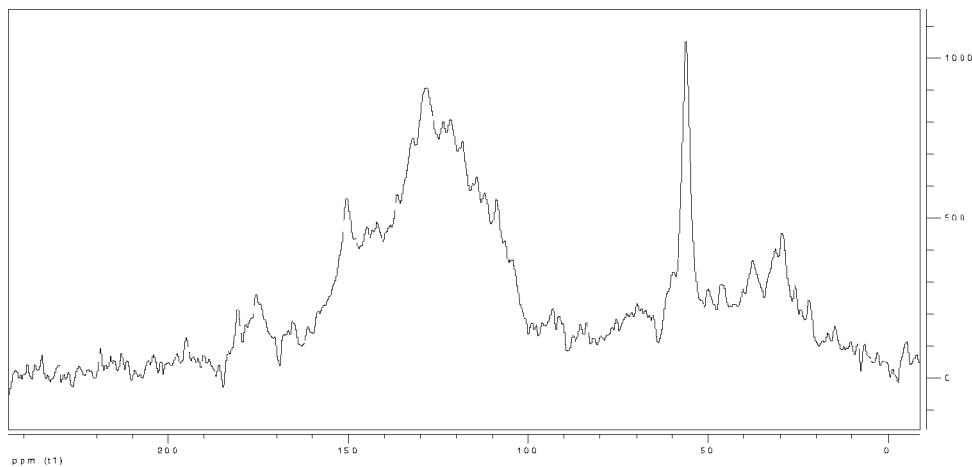
FIG. 3. $^{13}$C NMR spectrum of the polymer compound of benzene polycarboxylic acids of the present invention.

The structure of the polymer compound was analysed using $^{13}C$ NMR. The result is presented in Table 2 below and on FIG. 3.

TABLE 2

| Result of $^{13}C$ NMR analysis INTEGRAL INTENSITIES, % ± STANDARD DEVIATIONS | | | |
|---|---|---|---|
| 0-48 | 108-145 | 165-187 | 187-200 |
| 17.4 ± 1.7 | 41.1 ± 0.2 | 6.0 ± 0.5 | 2.0 ± 0 |

Figure 4A:
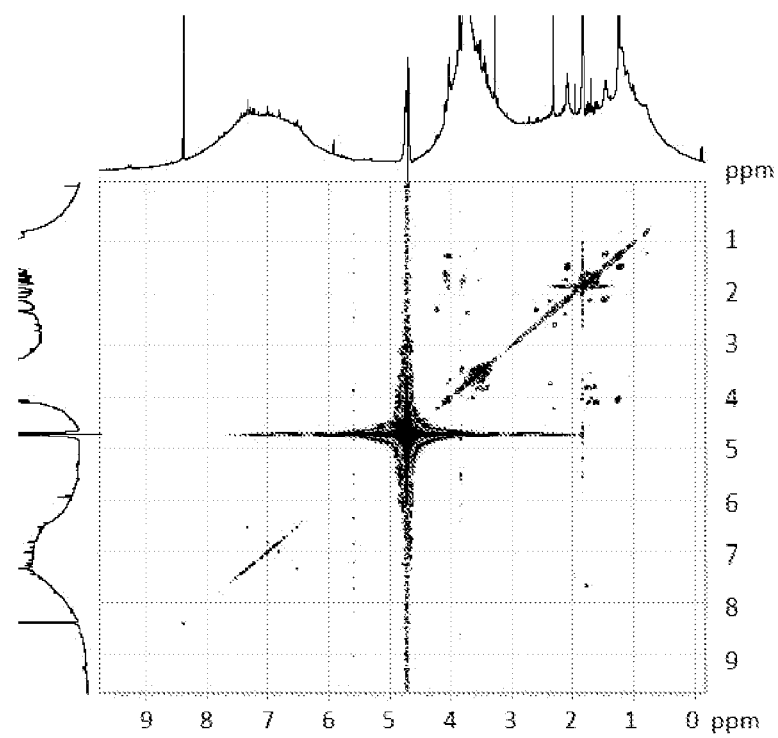
FIGS. 4A and 4B. Dimeric homo- and hetero-nuclear spectra of the polymer compound of benzene polycarboxylic acids of the present invention.
Figure 4A:
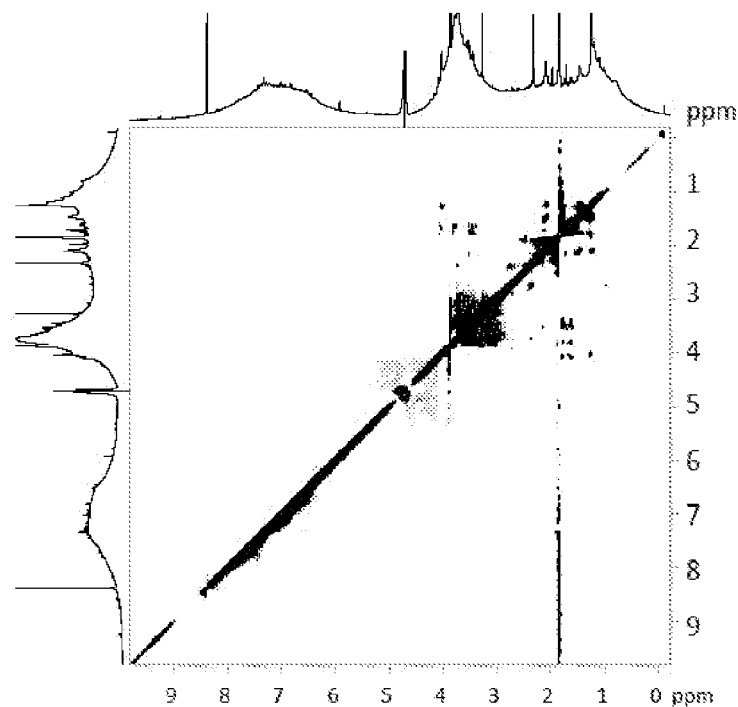
Figure 4B:
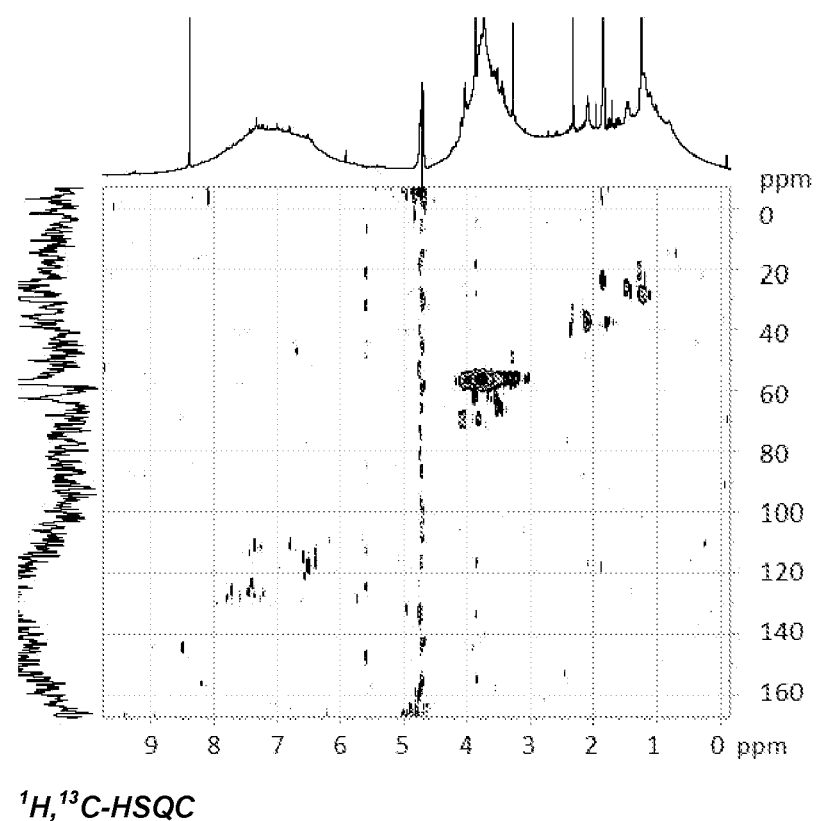

Dimeric homo- and hetero-nuclear spectra were additionally obtained for the polymer of the present invention (FIGS. 4A and 4B). Peak assignment results are presented in Table 3 below.

TABLE 3

| Dimeric homo- and hetero-nuclear spectra of the polymer of the present invention. | | | |
|---|---|---|---|
| F2 d (1H), ppm | F1 d (1H) or d (13C), ppm | Structural fragments | Description |
| $^{1}H,^{1}H$—COSY | | | |
| 1.2-1.5 | 1.2-1.5 | —CH$_n$—CH$_n$— | Alkyl |
| 1.2-1.8 | 3.7-4.2 | —CH$_n$—CH$_n$O— | Aliphatic alcohols |
| 1.5-2.2 | 1.5-2.2 | —CH$_n$—CH$_n$—C$_f$ | Alkyl, substituted with aromatic rings or carboxylic groups |
| 2.2-2.6 | 2.2-2.6 | C$_f$—CH$_n$—CH$_n$—C$_f$ | Alkyl, substituted with aromatic rings or carboxylic groups |
| 2.2-2.3 | 3.7; 4.2 | —CH$_n$O—CH$_n$—C$_f$ | Aliphatic alcohols, substituted with aromatic rings or carboxylic groups |
| 3.4-3.8 | 3.4-3.8 | —CH$_n$O—CH$_n$O— | Aliphatic alcohols |
| $^{1}H,^{1}H$—TOCSY | | | |
| 1.2-2.2 | 1.2-2.2 | —CH$_n$—...—CH$_n$— | Alkyl |
| 1.9-2.8 | 1.9-2.8 | C$_f$—CH$_n$—...—CH$_n$—C$_f$ | Alkyl, substituted with aromatic rings or carboxylic groups |
| 1.2-1.8 | 3.2-4.0 | —CH$_n$—...—CH$_n$O— | Aliphatic alcohols |
| 2.9-3.9 | 2.9-3.9 | —CH$_n$O—...—CH$_n$O— | |
| $^{2}H,^{13}C$-HSQC | | | |
| 1.1-1.9 | 17-32 | CH$_n$ | Alkyl |
| 1.7-2.4 | 32-42 | CH$_n$—C$_f$ | Alkyl, substituted with aromatic rings or carboxylic groups |
| 3.0-4.2 | 53-73 | CH$_n$O | Aliphatic alcohols, methoxyl |
| 7.2-7.8 | 110-130 | C$_{ar}$—OH | Phenolic |

According to data obtained from the NMR analysis, the polymer of this invention can be characterized as an aromatic core substituted with alkyl, methoxy, alcohol and hydroxy, as well as carboxy groups practically in all positions. As it can be seen from the Table 3, 4.5 to 6 atoms of aliphatic carbon correspond to 6 carbon atoms of aromatic carbon. At that, the following structural fragments are repeated: (C$_3$H$_2$O), (C$_2$H$_2$O), (CH$_2$).

Molecular weight of the claimed polymer was analysed using the gel-filtration method. Molecular weight of a fragment of the claimed polymer thus established constituted 1.5 kDa. The following structural formula was calculated based on the molecular weight, data from the elementary composition and the NMR analysis:

(C$_3$H$_2$O)$_{x1}$(C$_2$H$_2$O)$_{x2}$(CH$_2$)$_{x3}$, where x1≤12, x2≤9, x3≤33

Figure 5:
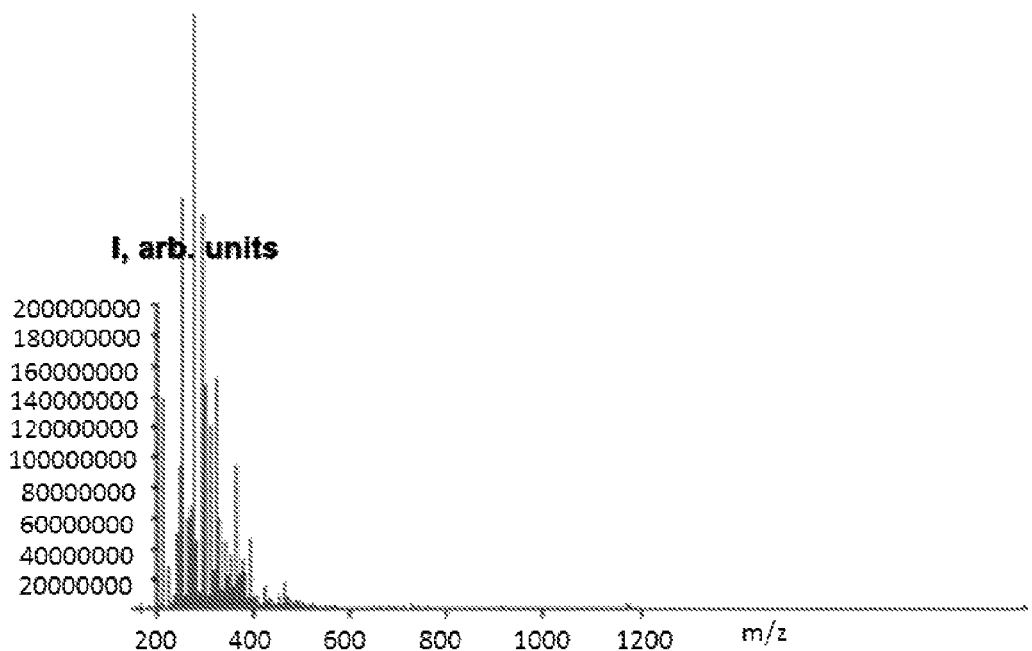
FIG. 5. FTICR MS spectrum of the polymer compound of benzene polycarboxylic acids of the present invention.

Monomers of the polymer of the present invention were also studied using Fourier Transform Ion Cyclotron Resonance Mass Spectrometry (FTICR-MS) (FIG. 5) (Table 4).

TABLE 4

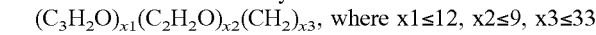

| Mass | Ab. | DBE | O/C | H/C | Brutto-formula | Name |
|---|---|---|---|---|---|---|
| Saturated aliphatic carboxylic acids and hydroxycarboxylic acids: | | | | | | |
| 227.2017 | 28015291 | 1.5 | 0.143 | 2 | C14H28O2 | Tetradecanoic |
| 255.2329 | 270821660 | 1.5 | 0.125 | 2 | C16H32O2 | hexadecanoic (palmitic) |
| 269.2486 | 59100516 | 1.5 | 0.118 | 2 | C17H34O2 | Heptadecanoic |
| 271.2279 | 67014157 | 1.5 | 0.188 | 2 | C16H32O3 | Hydroxyhexadecanoic |

TABLE 4-continued

High abundance monomers identified in the polymer of the present invention

| Mass | Ab. | DBE | O/C | H/C | Brutto-formula | Name |
|---|---|---|---|---|---|---|
| 283.2642 | 82866764 | 1.5 | 0.111 | 2 | C18H36O2 | Octadecanoic (stearic) |
| 299.2592 | 19214471 | 1.5 | 0.167 | 2 | C18H36O3 | Hydroxyoctadecanoic |
| 311.2956 | 19002772 | 1.5 | 0.1 | 2 | C20H39O2 | eicosanoic (arachidic) |
| 315.2541 | 18526027 | 1.5 | 0.222 | 2 | C18H36O4 | Dihydroxyoctadecanoic |
| 327.2905 | 16100520 | 1.5 | 0.15 | 2 | C20H39O3 | Hydroxyeicosanoic |
| 331.249 | 59016821 | 1.5 | 0.278 | 2 | C18H36O5 | Trihydrohyoctadecanoic |
| 339.3268 | 45615662 | 1.5 | 0.091 | 2 | C22H44O2 | docosanoic (behenic) |
| 353.3425 | 17780922 | 1.5 | 0.087 | 2 | C23H46O2 | Tricosanoic |
| 355.3218 | 37040552 | 1.5 | 0.136 | 2 | C22H44O3 | Hydroxydocosanoic |
| 367.3581 | 96229191 | 1.5 | 0.083 | 2 | C24H48O2 | tetracosanoic (lignoceric) |
| 381.3738 | 33496500 | 1.5 | 0.08 | 2 | C25H50O2 | pentacosanoic (behenic) |
| 383.3531 | 24354456 | 1.5 | 0.125 | 2 | C24H48O3 | Hydroxytetracosanoic |
| 395.3894 | 47932385 | 1.5 | 0.077 | 2 | C26H52O2 | hexacosanoic (cerotinic) |
| 397.3687 | 5537977 | 1.5 | 0.12 | 2 | C25H50O3 | Hydroxypentacosanoic |
| Monounsaturated aliphatic carboxylic acids and hydroxycarboxylic acids | | | | | | |
| 253.2173 | 94496905 | 2.5 | 0.125 | 1.875 | C16H30O2 | Hexadecenoic |
| 267.233 | 25781436 | 2.5 | 0.118 | 1.882 | C17H32O2 | Heptadecenoic |
| 281.2486 | 464974220 | 2.5 | 0.111 | 1.889 | C18H34O2 | octadecenoic (oleic) |
| 297.2435 | 147552180 | 2.5 | 0.167 | 1.889 | C18H34O3 | Hydroxyoctadecenoic |
| 309.2799 | 18244791 | 2.5 | 0.1 | 1.9 | C20H38O2 | Eicosenoic |
| 313.2384 | 67067499 | 2.5 | 0.222 | 1.889 | C18H34O4 | Dihydroxyoctadecenoic |
| 341.2697 | 20568853 | 2.5 | 0.2 | 1.9 | C20H38O4 | Dihydroxyeicosenoic |
| 345.2283 | 15144174 | 2.5 | 0.333 | 1.889 | C18H34O6 | Tetrahydroxyoctadecenoi |
| 369.301 | 22943789 | 2.5 | 0.182 | 1.909 | C22H42O4 | Dihydroxydocosenoic |
| Polyunsaturated aliphatic carboxylic acids (high abundance): | | | | | | |
| 299.2016 | 260077700 | 7.5 | 0.1 | 1.4 | C20H28O2 | 13-cis-Retinoic (Isotretinoin) |
| 275.2017 | 19416936 | 5.5 | 0.111 | 1.556 | C18H28O2 | Stearidonic acid 6Z,9Z,12Z,15Z-Octadecatetraenoic acid all-cis-6,9,12,15-Octadecatetraenoic acid |
| 277.2173 | 26976285 | 4.5 | 0.111 | 1.667 | C18H30O2 | γ-Linolenic acid cis,cis,cis-6,9,12-Octadecatrienoic acid |
| 293.2122 | 25597466 | 4.5 | 0.167 | 1.667 | C18H30O3 | (9R,13R)-2-oxo-5-pentyl-3-cyclopentene-1-octanoic acid |
| 309.2071 | 20667567 | 4.5 | 0.222 | 1.667 | C18H30O4 | 9S-hydroxyperoxy-10E,12Z,15Z-octadecatrienoic acid |

TABLE 4-continued

High abundance monomers identified in the polymer of the present invention

| Mass | Ab. | DBE | O/C | H/C | Brutto-formula | Name |
|---|---|---|---|---|---|---|
| 279.2329 | 90009812 | 3.5 | 0.111 | 1.778 | C18H32O2 | C13(S)-Hydroxyoctadeca-9Z,11E-dienoic acid 13(S)-HODE 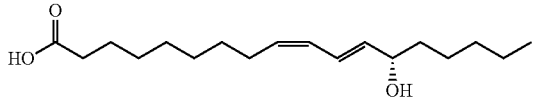 |
| 311.2228 | 120864140 | 3.5 | 0.222 | 1.778 | C18H32O4 | 10S,11S-epoxy-9S-hydroxy-12Z-octadecenoic acid 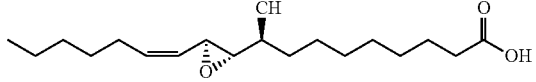 |
| 327.2177 | 55125151 | 3.5 | 0.278 | 1.778 | C18H32O5 | 9S,12S,13S-trihydroxy-10E,15Z-octadecadienoic acid 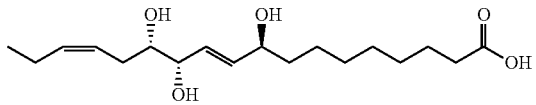 |
| 301.2173 | 148273490 | 6.5 | 0.1 | 1.5 | C20H30O2 | 5,6-Dehydroarachidonic acid<br>$CH^3(CH^2)^4(CH=CHCH^2)^3C\equiv CCH^2CH^2CH^2-\underset{O}{\overset{}{C}}-OH$ |
| 317.2122 | 21897255 | 6.5 | 0.15 | 1.5 | C20H30O3 | 15(S)-Hydroxy-(5Z,8Z,11Z,13E,17Z)-eicosapentaenoic acid 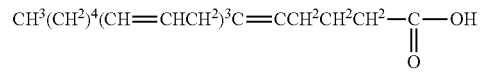 |
| Aromatic components (high abundance): | | | | | | |
| 273.0769 | 17358509 | 9.5 | 0.333 | 0.933 | C15H14O5 | 3-benzyloxy-4,5-dihydroxy-benzoic acid methyl ester 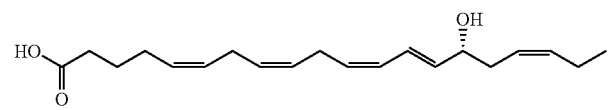 |
| 299.0561 | 12935282 | 11.5 | 0.375 | 0.75 | C16H12O6 | 5-(furan-2-carbonyloxy)-2-methyl-benzofuran-3-carboxylic acid methyl ester 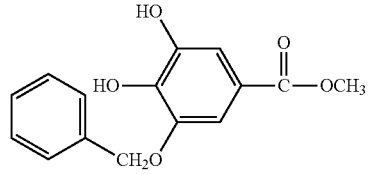 |
| 301.0718 | 54827333 | 10.5 | 0.375 | 0.875 | C16H14O6 | 2,6-dimethyl-benzo(1,2-b,4,5-b′)furan-3,7-dicarboxylic acid dimethyl ester 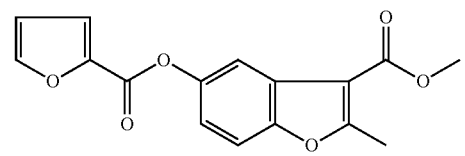 |

TABLE 4-continued
High abundance monomers identified in the polymer of the present invention
| Mass | Ab. | DBE | O/C | H/C | Brutto-formula | Name |
|---|---|---|---|---|---|---|
| 313.0718 | 10849880 | 11.5 | 0.353 | 0.824 | C17H14O6 | 5-(furan-2-carbonyloxy)-2-methyl-benzofuran-3-carboxylic acid ethyl ester |
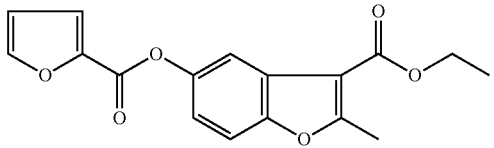
| 315.051 | 14450485 | 11.5 | 0.438 | 0.75 | C16H12O7 | Rhamnetin |
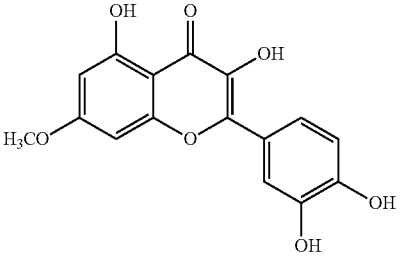
| 315.0874 | 33201977 | 10.5 | 0.353 | 0.941 | C17H16O6 | methyl ((4-methyl-6-oxo-6h-benzo(c)chromen-3-yl)oxy)acetate hydrate |
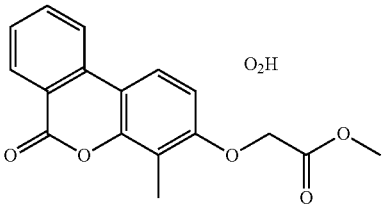
| 329.0667 | 14824822 | 11.5 | 0.412 | 0.824 | C17H14O7 | bis(2-(methoxycarbonyl)phenyl)carbonate |
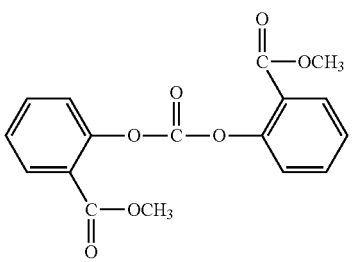
| 331.0823 | 29603426 | 10.5 | 0.412 | 0.941 | C17H16O7 | Sulochrin |
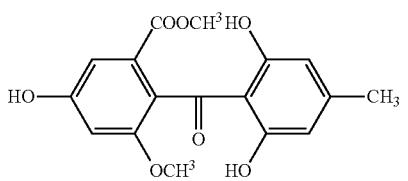

TABLE 4-continued

High abundance monomers identified in the polymer of the present invention

| Mass | Ab. | DBE | O/C | H/C | Brutto-formula | Name |
|---|---|---|---|---|---|---|
| 343.0823 | 13065197 | 11.5 | 0.389 | 0.889 | C18H16O7 | 2,6-Diacetyl-7,9-dihydroxy-8,9b-dimethyldibenzofuran-1,3(2H,9bH)-dione (+)-Usnic acid from Usnea dasypoga |

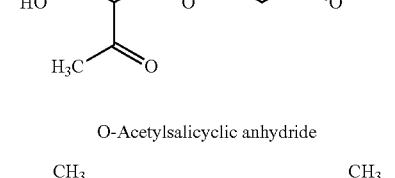

| 341.0667 | 11490045 | 12.5 | 0.389 | 0.778 | C18H14O7 | O-Acetylsalicyclic anhydride |

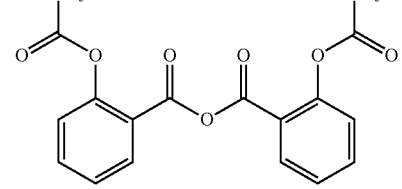

| 355.0823 | 12398987 | 12.5 | 0.368 | 0.842 | C19H16O7 | 4-ho-3-((6-ho-benzo(1,3)dioxol-5-yl)-(3-methoxy-phenyl)-methyl)-5h-furan-2-one |

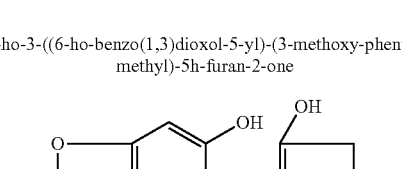

| 357.0616 | 10787448 | 12.5 | 0.444 | 0.778 | C18H14O8 | 2,3-bis-benzyloxy-succinic acid |

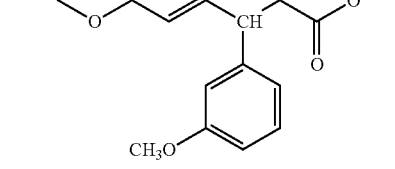

| 359.0773 | 11996010 | 11.5 | 0.444 | 0.889 | C18H16O8 | methyl 5-hydroxy-7,8-dimethoxy-1,3-dioxo-1,3,10,11-tetrahydrobenzo[5,6]cycloocta[1,2-c]furan-4-carboxylate |

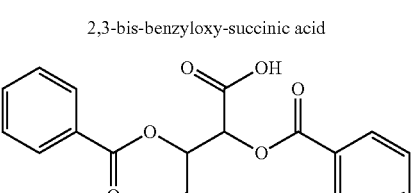

TABLE 4-continued

High abundance monomers identified in the polymer of the present invention

| Mass | Ab. | DBE | O/C | H/C | Brutto-formula | Name |
|---|---|---|---|---|---|---|
| 371.0772 | 15370496 | 12.5 | 0.421 | 0.842 | C19H16O8 | (1-methoxycarbonylmethoxy-6-oxo-6h-benzo(c)chromen-3-yloxy)-acetic acid me ester |
| 373.0929 | 13466093 | 11.5 | 0.421 | 0.947 | C19H18O8 | Atranorin |
| 423.1085 | 10753758 | 14.5 | 0.348 | 0.87 | C24H20O9 | Phenylpropanoid-Substituted Epicatechins |

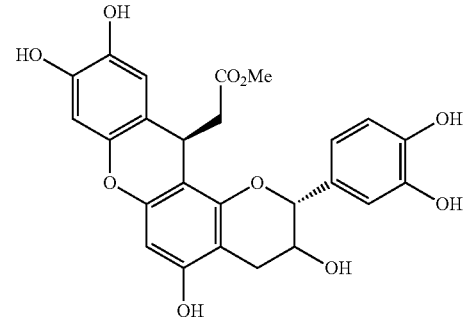

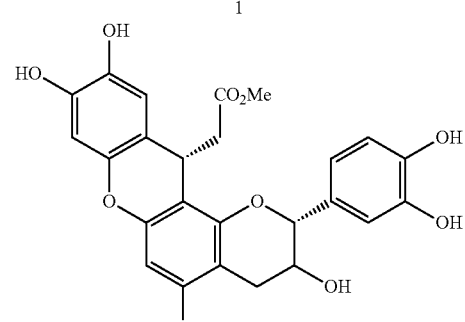

Experimental Data

Polymer compound of benzene polycarboxylic acids of the present invention was further diluted with distilled water to obtain different concentrations and was tested on peripheral blood mononuclear cells (PBMCs) consisting of lymphocytes (70-80%) and monocytes (20-30%) isolated from blood of healthy donors by Lymphoprep centrifugation.

Figure 7:
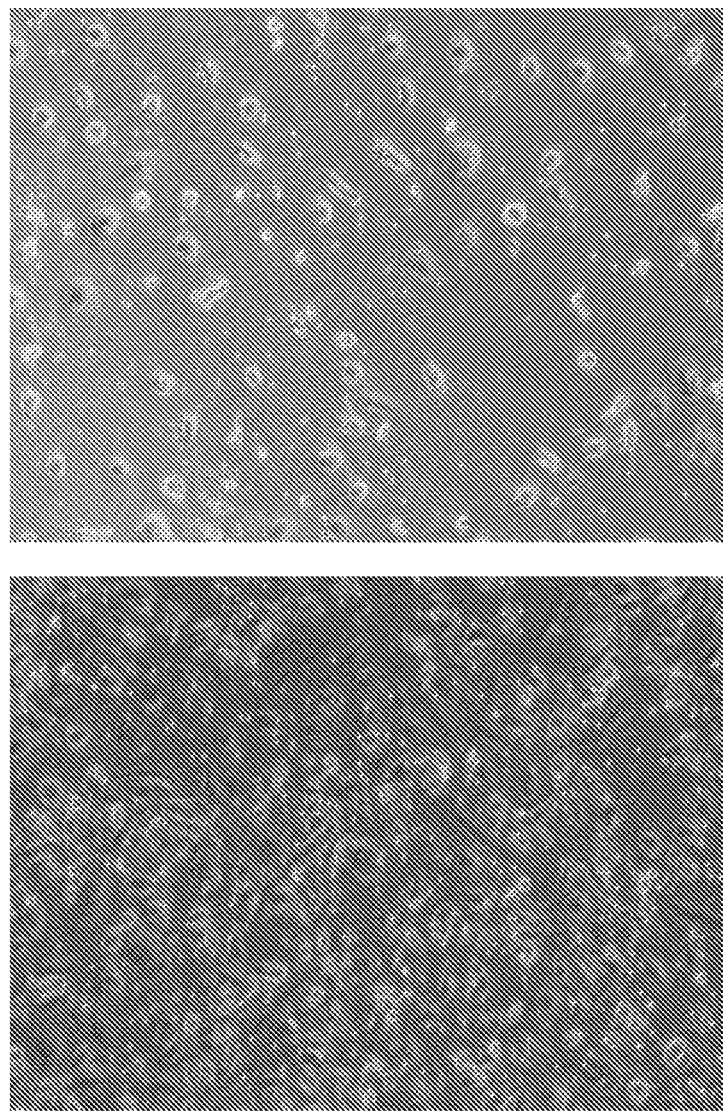
FIG. 7. Pictures of PBMC cells on day 15 of incubation in medium without addition of the polymer compound of benzene polycarboxylic acids (denoted as "a-control") and in the medium containing the polymer compound of benzene polycarboxylic acids of the present invention in the concentration of 215 μg/L of the medium (denoted as "b-polymer compound, 215 μg/L").
Figure 8:
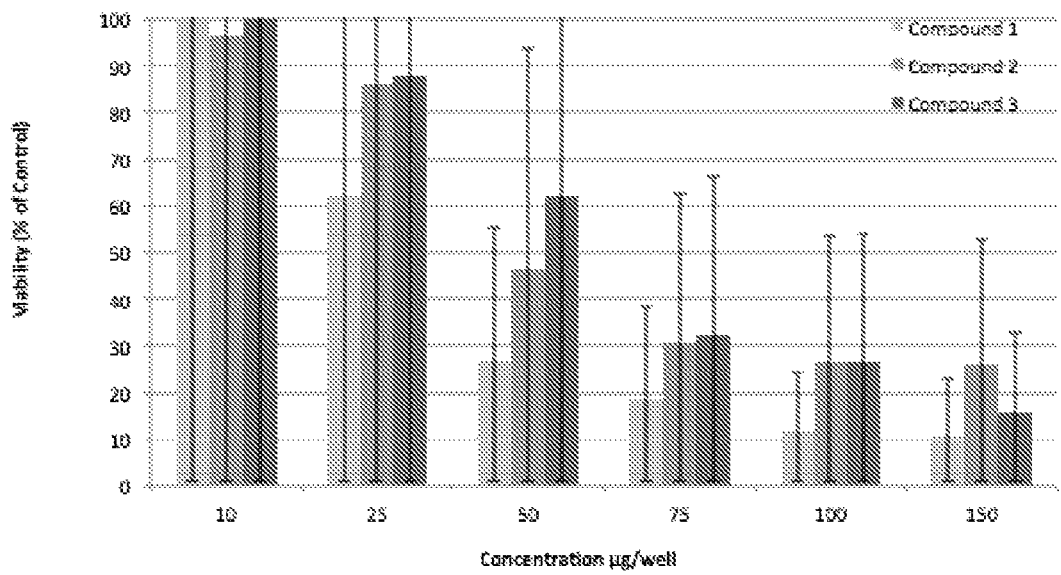
FIG. 8 shows viability data of MCF-7, human breast cancer cells after treatment with compounds of the present invention.
Figure 9:
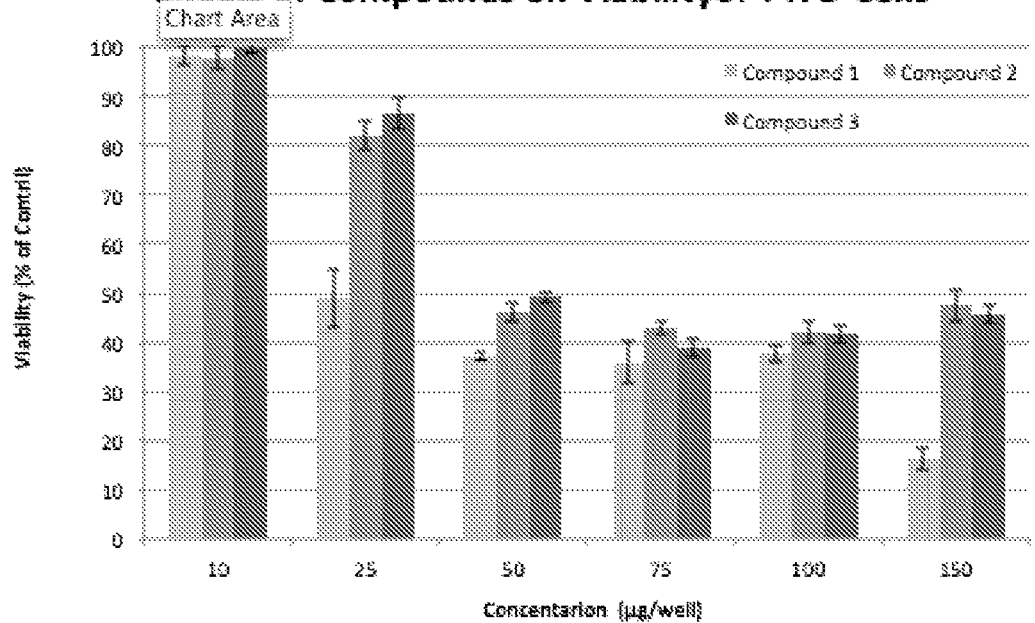
FIG. 9 shows viability data of T47-D, human breast cancer cells after treatment with compounds of the present invention.
Figure 10:
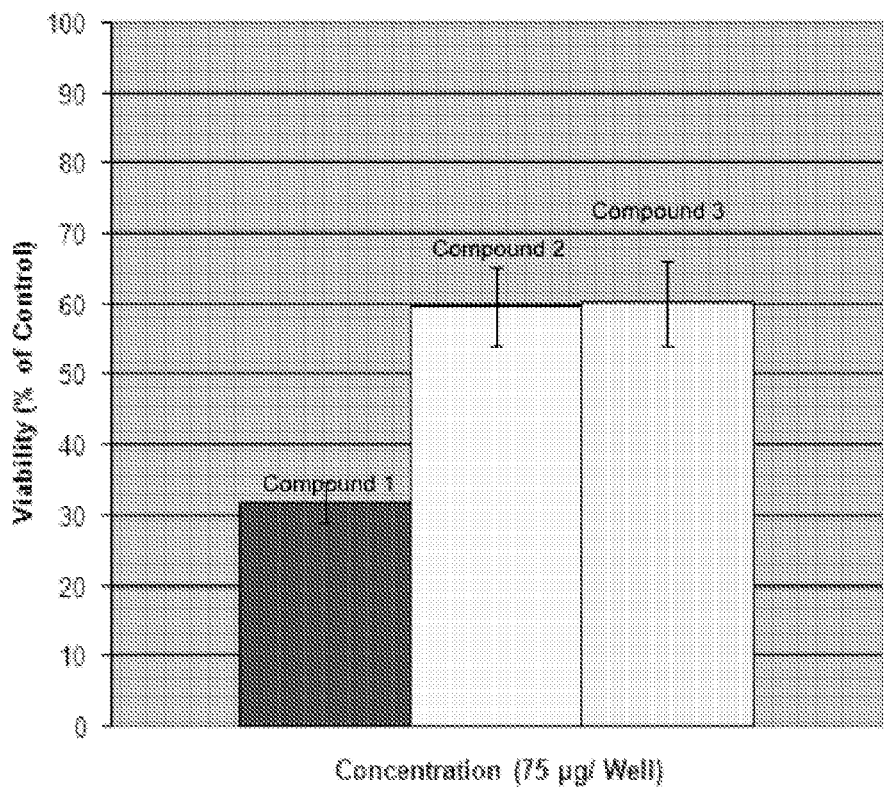
FIG. 10 shows viability data of PI45, human pancreatic cancer cells after treatment with compounds of the present invention.
Figure 11:
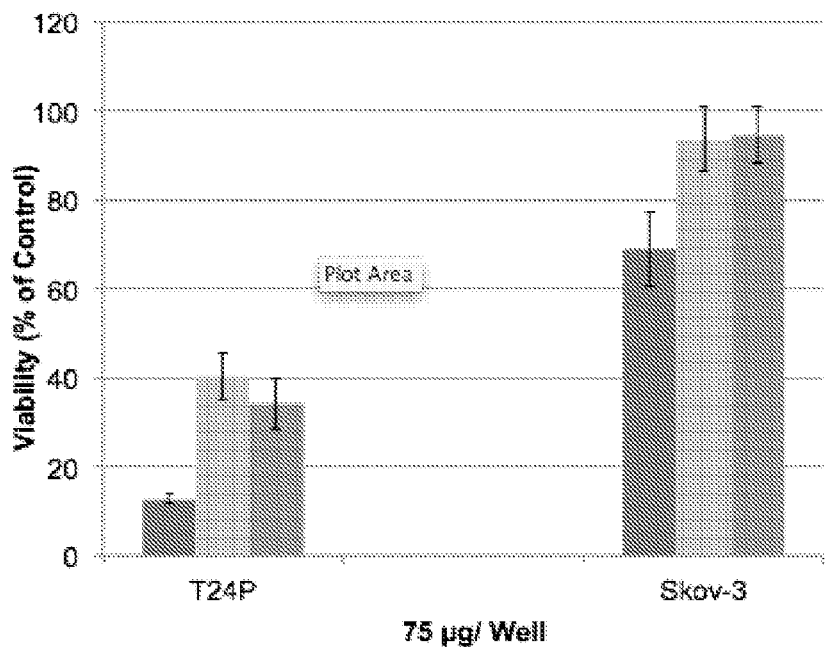
FIG. 11 shows viability data of T24P, human bladder cancer, and SKOV-3, human ovarian cancer cells, after treatment with compounds of the present invention.

It was established that after 15 days of incubation of the cell culture containing 215 µg/L of the polymer compound of benzene polycarboxylic acids of the present invention the latter exerted effect on PBMCs, manifested in increased motility of lymphocytes as well as increased persistence of monocytes, as illustrated on FIG. 7.

Example 2A

Method of Preparing an Anticancer Agent According to RU2182482 and Characterisation of the Said Anticancer Agent Preparation Humic acids prepared in Example 1A according to the method disclosed in RU2182482 were treated with 5% ammonia solution in the amount of 80 ml per 1 g of humic acids, heated on a water bath to remove excess of ammonia, filtered and mixed with 30 volume % of distilled water. Further, the resulting solution in the form of salts of humic acids was treated with potassium tetrachloroplatinate in the amount of 0.27 mass % per 1 g of humic acids salts and exposed to acoustic cavitation at 40 W/cm$^2$ and 22 kHz for 4 minutes. Water was used to adjust volume of the solution to 100 ml.

Experiment 2A-1

The anticancer agent thus obtained was administered subcutaneously in the amount of 62.5 mg/kg b.w. to mice with inoculated Ehrlich tumour. Tumour was inoculated subcutaneously in the amount of $10^7$ cells. Treatment was started 48 hours after tumour inoculation. Injections were given in the amount of 0.3 ml/mouse three times a week for 3 weeks (total of 9 injections). Control group was given isotonic sodium chloride solution according to the same dosing regimen. 60% survival (6 of 10 animals) and 50% tumour growth inhibition compared to the untreated control were registered in the experiment.

Mortality of animals was caused by toxicity of the platinum compound unbound to humic acids.

Example 2B

Method of Producing the Composite Substance Comprising Platinum (II) of the Present Invention and Characterisation of the Said Composite Substance Preparation Step a: 4.529 grams of dry polymer produced by the method described in Example 1B were diluted in 1 liter of distilled water and pH was adjusted to 9.2 using 10% ammonia solution. 0.8373 g of cis-diammineplatinum(II) dichloride was added to the solution. The resulting solution was subjected to ultrasound treatment at 3.5 W/cm$^3$ and 22 kHz until the content of unbound platinum fell below 25% of the original quantity.

Method of Detection of Unbound Platinum

Completeness of formation of the platinum complex was controlled using cellulose dialysis membranes with standard 500-1000 Da pores. This size of the pores makes it possible for the platinum compound to penetrate through the membrane, while it prevents the claimed polymer of 1500 Da and consequently its complex with the platinum from doing the same.

To perform the test dialysis tubes were filled with 8 ml samples of the composite substance collected during the ultrasound treatment and dipped into vessels filled with distilled water for 4 hours to accommodate the dialysis.

0.8373 g of cis-diammineplatinum(II) dichloride were diluted in 1 liter of distilled water to obtain model solution (control solution). Amount of platinum transferred from the model solution into dialysate was taken as 100%.

Concentration of free platinum measured in dialysate of the model solution constituted 76 mg/l (100%), while concentration of the same in dialysate of the composite substance of this invention constituted 18 mg/l (24%).

Step b: Further, the reaction mixture, comprising the polymer compound of benzene polycarboxylic acids and cis-diammineplatinum(II) dichloride was subjected to thermostating at 40° C. for 24 hours to accommodate completion of formation of the desired complex. The thermostating was continued until concentration of unbound platinum (established with the above-described method) fell below 10% of the quantity added on step a.

Step c: Further, the crude composite substance of step b was purified from mechanical inclusions using 10.0 μm polypropylene filter and then used for preparation of a pharmaceutical composition as described in Example 3.

Experiment 2B-1

The composite substance thus obtained was administered subcutaneously in the amount of 62.5 mg/kg b.w. to animals with inoculated Ehrlich tumour. Tumour was inoculated subcutaneously in the amount of $10^7$ cells. Treatment was started 48 hours after tumour inoculation. Injections were given in the amount of 0.3 ml/mouse three times a week for 3 weeks (total of 9 injections). Control group was given isotonic sodium chloride solution according to the same dosing regimen. 100% survival (10 of 10 animals) and 65% tumour growth inhibition compared to the untreated control were registered in the experiment.

Better safety and efficacy of the composite substance compared to the anticancer agent of RU2182482 were the result of a better complexation of the platinum compound within the claimed composite substance.

Characterisation

Figure 6:
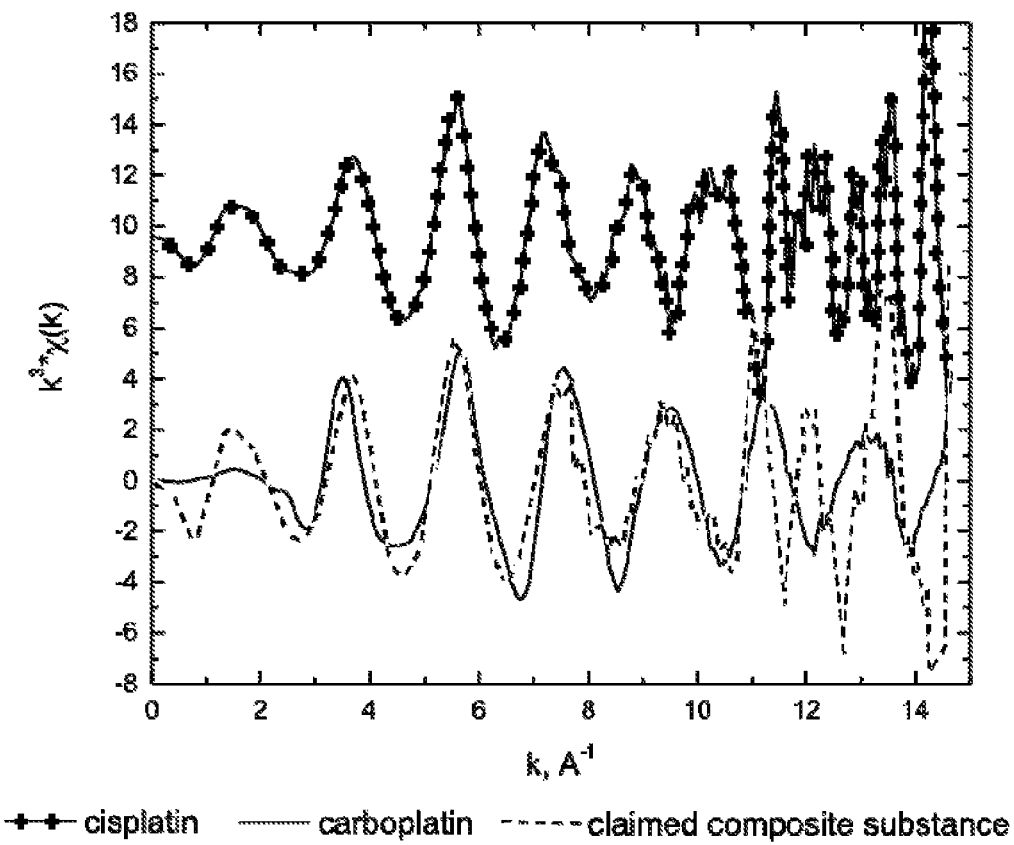
FIG. 6. Extended X-ray Absorption Fine Structure (m) spectra of a composite substance comprising polymer compound of benzene polycarboxylic acids of the present invention and cis-diammineplatinum(II) dichloride, the inorganic cis-diammineplatinum(II) dichloride (denoted on the figure as "Cisplatin") and cis-diammine(cyclobutane-1,1-dicarboxylate-O,O')platinum(II) (denoted on the figure as "Carboplatin").

The formation of the novel complex of the polymer compound of benzene polycarboxylic acids with cis-diammineplatinum (II) dichloride was further investigated using Extended X-ray Absorption Fine Structure analysis (EXAFS) (see FIG. 6). Significant differences between the claimed composite substance comprising the polymer compound of benzene polycarboxylic acids of the present invention and cis-diammineplatinum(II) dichloride, the inorganic cis-diammineplatinum(II) dichloride (denoted in the spectrum as "Cisplatin") and cis-diammine(cyclobutane-1,1-dicarboxylate-O,O')platinum(II) (denoted on the figure as "Carboplatin") can be seen on the EXAFS spectrum.

The composite substance of the present invention is characterized by the following characteristic absorption bands of the IR spectrum: 3400-3600 cm$^{-1}$, 2800-3000 cm$^{-1}$, 1500-1700 cm$^{-1}$, 1410 cm$^{-1}$, 1250-1300 cm$^{-1}$ and 1050 cm$^{-1}$, where the intensity of the 3400-3600 cm$^{-1}$, 1500-1700 cm$^{-1}$, 1410 cm$^{-1}$ and 1250-1300 cm$^{-1}$ bands of the composite substance is smaller than that of the polymer compound of the benzene polycarboxylic acids.

Based on the data derived with the $^{13}$C NMR and EXAFS methods the following brutto formula of the composite substance was calculated: $(C_3H_2O)_{x1}(C_2H_2O)_{x2}(CH_2)_{x3}(Pt$ (NH$_3$)$_2$)$_{x4}$, where $x_1$, $x_2$, $x_3$ and $x_4$ are the coefficients representing any natural positive full or fractional number.

Example 3

Description of Nonclinical and Clinical Data that Supports Use of Pharmaceutical Composition Based on the Composite Substance Comprising the Water-Soluble Polymer Compound of Benzene Polycarboxylic Acids and a Pt Compound and Characterisation of the Same Preparation The 0.5% composite substance prepared in accordance with Example 2B was used as the basis for obtaining a pharmaceutical composition additionally comprising such excipients as the solvent in the form of isotonic sodium chloride solution to obtain 0.05% pharmaceutical composition and the buffering agent in the form of hydrochloric acid to obtain pH of 7 to 8. Pharmaceutical composition was obtained through mechanical stirring of the composite substance and excipients at constant monitoring of the pH. Pharmaceutical composition was additionally purified using sterilizing filtration.

The pharmaceutical composition thus obtained can be used for parenteral (subcutaneous or intramuscular) administration.

Characterisation

Pharmaceutical composition was characterized by the methods described in the 6$^{th}$ edition of the European Pharmacopoeia, as follows:

Description: transparent, dark-brown liquid
pH: 7.27
Identity: characteristic IR absorption bands at 3400-3600 cm$^{-1}$, 2800-3000 cm$^{-1}$, 1500-1700 cm$^{-1}$, 1410 cm$^{-1}$, 1250-1300 cm$^{-1}$ and 1050 cm$^{-1}$, with intensity of the peaks at 3400-3600 cm$^{-1}$, 1500-1700 cm$^{-1}$, 1410 cm$^{-1}$ and 1250-1300 cm$^{-1}$ smaller than that of the polymer compound of the benzene polycarboxylic acids.
Content of platinum: 0.0049%
Sterility: sterile
Toxicity: non-toxic at 0.1 mg per mouse
Pyrogenicity: non-pyrogenic in dose 1.3 mg/kg b.w., intramuscular (rabbit test)

Non-Clinical Data

Antitumor efficacy of the claimed pharmaceutical composition was evaluated in autochthonous spontaneous mammary tumours in HER-2/neu female mice characterized by elevated levels of expression of HER-2/neu oncogene, epidermal growth factor and high probability of spontaneous development of multiple mammary neoplasms.

According to the chosen design, when diameter of mammary tumours has grown to at least 5 mm animals were randomized between control and experiment groups. The claimed pharmaceutical composition was injected subcutaneously in two doses (62.5 mg/kg b.w. and 3.0 mg/kg b.w.) 3 times a week until decease of animals.

Percentage of 7-14 days remissions in animals treated with 62.5 mg/kg b.w. or 3 mg/kg b.w. of the claimed pharmaceutical composition constituted 13% and 12% respectively (results were statistically significant) against 0% in the control group. This is a good indication of efficacy of the claimed pharmaceutical composition in treatment of mammary tumours that can be extrapolated to human beings and non-food producing animal species.

Clinical Data

Phase lb clinical study of the claimed drug was performed in 8 patients with metastatic breast cancer. Patients were given 1 daily injection of the drug for 32 days. Evaluated cumulative dose-window constituted from 0.96 mg/kg b.w. to 1.12 mg/kg b.w.

The following results were obtained using the claimed pharmaceutical composition: 1 complete response (disappearance of all metastases), 1 partial response (greater than 25% reduction of size of metastases), 3 stable diseases (change of the size of metastases between −25% and 25%) and 3 progressive diseases (larger than 25% increase of the size of metastases).

These results are a good indication of clinical efficacy of the claimed pharmaceutical composition in treatment of metastatic breast cancer.

Altogether 78 adverse events were registered in the study. None of the registered adverse events was serious. Adverse events were mainly mild or moderate and only 2% of the 78 adverse events were related to the claimed pharmaceutical composition.

Besides, reduction of the number of side effects was observed in response to increase of the treatment dose of the claimed pharmaceutical composition. This data is a good indication of outstanding safety of the claimed pharmaceutical composition and its potential in palliative therapy of, for instance, terminal patients.

It was additionally established that the claimed pharmaceutical composition aids in normalisation of blood parameters. Thus, by the end of the follow up period the following blood parameters were normalized: haemoglobin in 2 of the 4 patients, erythrocytes in 2 of the 3 patients, thrombocytes in 1 of the 3 patients, leucocytes in 3 of the 5 patients, neutrophils in 3 of the 3 patients and lymphocytes in 1 patient, compared to the levels registered at the screening.

This data is a good indication that the claimed pharmaceutical composition can be efficiently used for modification of the main disease such as, for instance, cancer.

Example 4

Method of Producing the Composite Substance Comprising the Water-Soluble Polymer Compound of Benzene Polycarboxylic Acids and a Molybdenum Compound and Characterisation of the Said Composite Substance Step a: 15 grams of dry polymer produced by the method described in Example 1B were diluted in 1 liter of distilled water, pH was adjusted to 9.2 using approximately 15 ml of 10% ammonia solution. Further, the solution was heated to 60° C. and stirred for 1.5 hours to remove excess ammonia. 5 g of ammonium molybdate tetrahydrate were added and the resulting solution was subjected to ultrasound treatment at 3.5 W/cm$^3$ and 22 kHz until the content of unbound molybdenum fell below 25% of the original quantity.

Method of Detection of Unbound Molybdenum:
Completeness of formation of the molybdenum complex was controlled using cellulose dialysis membranes with standard 500-1000 Da pores. This size of the pores allows the molybdenum compound to leave through the membrane, while it prevents the claimed polymer of 1500 Da and consequently its complex with molybdenum from doing the same.
To perform the test dialysis tubes were filled with 8 ml samples of the composite substance collected during the ultrasound treatment and dipped into vessels filled with distilled water for 4 hours to accommodate the dialysis.

5 g of ammonium molybdate tetrahydrate were diluted in 1 liter of distilled water to obtain model solution (control solution). Amount of molybdenum transferred from the model solution into dialysate was taken as 100%.

Concentration of free/unbound molybdenum in dialysate of the model solution constituted 52 mg/l (100%), while concentration of the same in dialysate of the composite substance of this invention constituted 11 mg/l (21%).

Step b: Further, the composite substance comprising the polymer compound of benzene polycarboxylic acids and ammonium molybdate tetrahydrate of step a was subjected to thermostating at 40° C. for 24 hours to accommodate completion of formation of the desired complex. The thermostating was continued until concentration of unbound molybdenum (established with the above-described method) fell below 10% of the quantity added on step a.

Step c: The crude composite substance of step b was purified from mechanical inclusions using 10.0 µm polypropylene filter and used for preparation of a pharmaceutical composition as described in Example 5.

Characterisation

Composite substance is characterized by the following characteristic absorption bands of the IR spectrum: 3400-3600 cm$^{-1}$, 2800-3000 cm$^{-1}$, 1500-1700 cm$^{-1}$, 1410 cm$^{-1}$, 1250-1300 cm$^{-1}$ and 1050 cm$^{-1}$, where the intensity of the 3400-3600 cm$^{-1}$, 1500-1700 cm$^{-1}$, 1410 cm$^{-1}$ and 1250-1300 cm$^{-1}$ bands of the composite substance is smaller than that of the polymer compound of the benzene polycarboxylic acids.

Based on the data derived with $^{13}$C NMR method the following brutto formula of the composite substance was calculated:

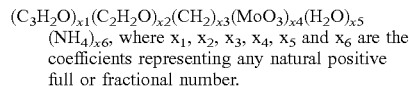

$(C_3H_2O)_{x1}(C_2H_2O)_{x2}(CH_2)_{x3}(MoO_3)_{x4}(H_2O)_{x5}(NH_4)_{x6}$, where $x_1$, $x_2$, $x_3$, $x_4$, $x_5$ and $x_6$ are the coefficients representing any natural positive full or fractional number.

Example 5

Description of Experimental Data that Supports Clinical Use of Pharmaceutical Composition Based on the Composite Substance Comprising the Water-Soluble Polymer Compound of Benzene Polycarboxylic Acids and a Molybdenum Compound and Characterisation of the Same Preparation The composite substance prepared in accordance with Example 4 was used as the basis for obtaining a pharmaceutical composition additionally comprising distilled water as a solvent. For that 0.55% composite substance was mixed with distilled water in 1:40 ratio and stirred mechanically. The pharmaceutical composition thus obtained can be used for peroral administration.

Characterisation

Pharmaceutical composition was characterized by the methods described in the 6$^{th}$ edition of the European Pharmacopoeia as follows:

Description: Non-transparent, dark-brown liquid
pH: 8.27
Identity: IR with absorbance bands in: 3400-3600 cm$^{-1}$, 2800-3000 cm$^{-1}$, 1500-1700 cm$^{-1}$, 1410 cm$^{-1}$, 1250-1300 cm$^{-1}$ and 1050 cm$^{-1}$ regions with intensity of 3400-3600 cm$^{-1}$, 1500-1700 cm$^{-1}$, 1410 cm$^{-1}$ and 1250-1300 cm$^{-1}$ bands of the pharmaceutical composition smaller than that of the polymer compound of the benzene polycarboxylic acids.

Bioburden: less than 100 cfu/g
Toxicity: non-toxic in dose 0.1 mg per mouse
Pyrogenicity: non-pyrogenic in dose 1.3 mg/kg b.w., intramuscular (rabbit test)

Experimental Data

Pharmaceutical composition based on the composite substance comprising the water-soluble polymer compound of benzene polycarboxylic acids and a molybdenum compound was further diluted with distilled water to obtain different concentrations and was tested on peripheral blood mononuclear cells (PBMCs) consisting of lymphocytes (70-80%) and monocytes (20-30%) isolated from blood of healthy donors by Lymphoprep centrifugation.

It was established that after 11 days of incubation of the cell culture containing 35 and 215 µg/L of the pharmaceutical composition the latter exerted effect on PBMCs, manifested in increased motility of lymphocytes as well as increased persistence of monocytes.

Effect of the pharmaceutical composition on a panel of cytokines produced by peripheral blood mononuclear cells (PBMCs) was assessed in the same series of experiments. It was established that after 11 days of incubation of the cell culture production of INF-gamma grows from 0-75 pg/ml in the control group to 2000-3000 pg/ml in groups treated with the pharmaceutical composition; production of TNF-alfa grows from 0 in the control group to 400-650 pg/ml in groups treated with the pharmaceutical composition.

This data is a good indication that the pharmaceutical composition can be efficiently used for prophylaxis and treatment of diseases associated with cell cycle disruption (for example, carcinogenesis induced by radiation or caused by natural ageing of cells).

Example 6

Description of Experimental Data that Supports Clinical Use of a Pharmaceutical Composition Based on the Composite Substance Comprising the Water-Soluble Polymer Compound of Benzenepolycarboxylic Acids and a Molybdenum Compound in Reducing/Minimising Side Effects Associated with Conventional Radiotherapy or Chemotherapy Patient Characteristics:

The patient of this study was a 64 years old woman with a long history of gastrointestinal problems. Colon cancer with local metastasis to the lymph nodes was diagnosed in May 2012 and surgery was recommended and performed in June same year. Due to different circumstances, she had to be re operated two times. The patient was first time evaluated for start chemotherapy by the end of August.

Results and Procedure:

The laboratory results related to the first evaluation detected a substantially low Serum Albumin in combination with low Haemoglobin, Leucocytes, Neutrophil granulocytes and Lymphocytes. Additionally, the laboratory analysis detected reduced Eosinophil, ALAT, ASAT and Alkaline Phosphatases (Table 5). The responsible Oncologist avoided start of Chemotherapy and new evaluation had to be performed within two weeks. During this period, the patient was daily given 20 ml of a pharmaceutical composition comprising the new benzene polycarboxylic acids complex with molybdenum. The composition was administered orally. The laboratory results taken at the second evaluation showed normalization in Albumin; substantially increase in the level of Haemoglobin, Leucocytes, Neutrophil granulocytes and Lymphocytes and Eosinophil. Additionally, both ALAT and ASAT levels were increased. The Chemotherapy was started immediately.

Chemotherapy Treatment:

The patient was given two days injections 12 time with a rest period of two weeks between each chemotherapy treatment. Blood samples for laboratory analysis were taken after additional treatment with the composition of the present invention compared to the treatment before and after in which the patient was also treated with the composition of the present invention.

Similar pattern is also detected with regards to Haemoglobin, Leucocytes, Granulocytes, Lymphocytes and Eosinophil. All these variables were low before start of chemotherapy, but increase substantially with additional oral treatment with the composition of the present invention in 10 days. These obtained levels were found nearly unchanged during the first chemotherapy treatment period with additional treatment with the composition of the present invention.

TABLE 5

Development in some laboratory variables during the seven first chemotherapy treatment periods. The column given in bold indicate the situation without additional treatment with the composition of the present invention

| | | Chemotherapy treatment period | | | | | | | |
|---|---|---|---|---|---|---|---|---|---|
| Variables | Before | 0 | 1 | 2 | 3 | 4 | 5 | 6 | 7 |
| Add. treatment* | no | yes | yes | no | yes | yes | yes | no | yes |
| Haemoglobin | 9.4 | 11.0 | 11.3 | 10.3 | 10.8 | 10.9 | 10.2 | 10.6 | 10.9 |
| Leucocytes | 4.0 | 7.6 | 7.2 | 3.8 | 5.8 | 7.1 | 4.0 | 3.7 | 4.8 |
| Granulocytes | 2.4 | 5.1 | 4.4 | 2.2 | 3.7 | 4.9 | 2.2 | 2.2 | 3.2 |
| Lymphocytes | 1.0 | 1.6 | 2.0 | 1.0 | 1.4 | 1.4 | 1.2 | 0.9 | 1.1 |
| Eosinophil | 0.03 | 0.09 | 0.13 | 0.11 | 0.07 | 0.14 | 0.19 | 0.12 | 0.13 |
| ALAT | 28 | 89 | 66 | 55 | | 49 | | 29 | |
| ASAT | 25 | 111 | 43 | 51 | | | | | |
| Albumin | 28 | 39 | 40 | 37 | | 41 | | 38 | 39 |

*Add treatment indicates whether the composition of the present invention was administered together with chemotherapy; "yes" indicates that the composition of the present invention was administered in that period, whereas "no" indicates that the composition of the present invention was not administered in that period each treatment. Additionally, the patient filled out the Quality of Life (QoL) questionnaire C-30 in the mid part of some of the rest periods.

The patient was given 20 ml orally administrated composition of the present invention (i.e. the composite substance comprising the water-soluble polymer compound of benzenepolycarboxylic acids and a molybdenum compound) two weeks before and the first week after the first two days of injection.

One week before and one week after the second injection period, no composition of the present invention was available. The treatment with the composition of the present invention was restarted one week after the second injection period and given daily before and after the following three injection periods. One week before the sixth injection period, the patient again runs out of composition of the present invention. This additional treatment was again started just before the seventh treatment period and out the remaining part of the 12 chemotherapy treatment periods.

The QoL questionnaire C-30 was filled out by the patient after the first treatment period and the second treatment period. Additionally, the questionnaire was filled out after the fifth, the sixth and the seventh treatment period.

Results

Laboratory Variable:

Serum Albumin was found to low for starting the chemotherapy treatment. Initially, it was found as low as 28 (Table 5), but increased to 39 after 10 days treatment with the composition of the present invention. This value was kept also during the first chemotherapy treatment period with additional treatment with the composition of the present invention. The Albumin was slightly reduced during both the second and the sixth chemotherapy treatment without The second chemotherapy treatment period was performed without administration of the composition of the present invention and all the above described variables were again found reduced. The three following chemotherapy periods were performed with additional administration of the composition of the present invention and Haemoglobin, Leucocytes, Granulocytes and Lymphocytes increased again to the previous levels. Nearly the similar pattern was also detected for Eosinophil except for the third treatment period. The sixth chemotherapy treatment period was as the second also performed without additional administration of the composition of the present invention and nearly the same happen again.

ALAT and ASAT were only measured before start and during the two first chemotherapy treatment periods. However, the same pattern as described for the haematological variables above was indicated.

Quality of Life Questionnaire C-30: The sum of C-30 was found reduced with 53% from the rest period after the first chemotherapy treatment with additional administration of the composition of the present invention to the rest period after the second chemotherapy treatment without additional administration of the composition of the present invention. The similar pattern was also detected in the rest period after the fifth, sixth and seventh chemotherapy treatment. From the fifth with additional administration of the composition of the present invention to the sixth without, the Sum C-30 was reduced with 48% and increase with 58% from the sixth to the seventh with additional administration of the composition of the present invention.

Conclusion: Even though this study was only an unstructured case report, it clearly indicates a beneficial effect of compositions of the present invention as a possible supplement treatment to chemotherapy treatment.

Example 7

Study of Viability of Cancer Cells when Treated with Compounds of the Present Invention The cells studied in this study are
MCF-7, human breast cancer cells (well differentiated)
T47-D human breast cancer cells (poorly differentiated)
Pl45 human pancreatic cells (poorly differentiated)
T24P human bladder cancer (poorly differentiated)
SKOV human ovarian cancer cells (poorly differentiated)
HCT116 human colorectal cancer cells
Fadu human head and neck cancer cells
The cells were treated with:
the water-soluble polymer compound of benzenepolycarboxylic acids (referred to in FIGS. 8-13 as "Compound 2"),
composite substance comprising the water-soluble polymer compound of benzenepolycarboxylic acids and a platinum compound (referred to in FIGS. 8-13 as "Compound 1"), and
composite substance, comprising the water-soluble polymer compound of benzenepolycarboxylic acids and a molybdenum compound (referred to in FIGS. 8-13 as "Compound 3") in different amounts (10-200 μg/well) for 72 hours.

Cell Viability

Cells were plated into 96-well plates ($5 \times 10^4$ cells/nil), and on the second day the medium were replaced by medium containing varying concentrations of the compounds/composite substances. After 72 and 96 hours, cell viability was determined using the XTT assay according to the protocol accompanying the kit.

The results are shown in FIGS. 8-11.

The results show that all three compound/composite substances affect the viability of all cell lines. The viability was reduced from 40% to 90% depending on the cell line investigated. The most effective killing effect was seen in human colonic human and human head and neck cancer cells lines and the lowest killing effect was observed by the test substances in ovarian and liver cancer cell lines. See table 6 below.

The results show no signs of cellular damage. The same release of LDH from control cells as well as from cells treated with the test substances; i.e. the substances are non-toxic. Cellular damage, such as necrosis, causes an elevation of the LDH concentration in the medium. The integrity of the plasma membrane following treatment was determined by measuring LDH activity released into the culture medium. The enzyme activity was measured using a spectrophotometric method (Moran and Schnellmann 1996).

The invention claimed is:

1. A water-soluble polymer compound of benzene polycarboxylic acids having an elemental composition of 62-67% C, 3.8-4.2% H, 29-34% O, and less than 0.2% N per dry weight and where the sum of other elements is no more than 1% per dry weight.

2. The compound according to claim 1,
wherein the compound has $^{13}$C NMR characteristic peaks at 15-22% in the 0-48 ppm range, 30-42% in the 108-145 ppm range, 5-13% in the 165-187 ppm range and 2-8% in the 187-220 ppm range; and/or
wherein the compound comprises no more than 1% low-molecular impurities identified by $^{13}$C NMR characteristic peaks at 168.5, 171, 173, 181-182 ppm; and/or
wherein the compound has IR absorption bands at 3400-3600 $cm^{-1}$, 2800-3000 $cm^{-1}$, 1500-1700 $cm^{-1}$, 1410 $cm^{-1}$, 1250-1300 $cm^{-1}$ and 1050 $cm^{-1}$.

3. The compound according to claim 1, wherein the compound comprises at least one monomer from each of the groups: saturated aliphatic carboxylic acids, saturated aliphatic hydroxycarboxylic acids, monounsaturated aliphatic carboxylic acids, monounsaturated aliphatic hydroxycarboxylic acids, polyunsaturated aliphatic carboxylic acids and aromatic components.

4. A process for preparing the water-soluble polymer compound of benzene polycarboxylic acids according to claim 1, comprising:
a) providing a lignin-containing starting raw material, which is produced from conifer trees and has a pH from 5.5 to 7, a moisture content from 50 to 70% and comprises no more than 32% of polysaccharides, no less than 66% of lignin and no more than 2% of water-soluble compounds,

TABLE 6

Estimated IC50 values for the composite substance comprising platinum

| Cell line | T47D (Breast) | MCF-7 (Breast) | HEPG2 (Liver) | T24P (Bladder) | Skov3 (Ovary) | PL45 (Pancrease) | HCT116 (Colon) | Fadu (Head & Neck) |
|---|---|---|---|---|---|---|---|---|
| IC50 (μg/ml) | ~490 | ~370 | ~1700 | ~500 | ~1000 | ~500 | ~150 | ~150 |

Cytotoxic Activity by Measuring Lactate Dehydrogenase (LDH)

The integrity of the plasma membrane was determined by measuring LDH activity released into the culture medium. LDH activity was monitored following the oxidation of NADH as the decrease in absorbance at 334 nm. The percentage of LDH released was defined as the ratio of LDH activity in the supernatant to the sum of LDH amount released plus the activity measured in the cell lysate.

Figure 12:
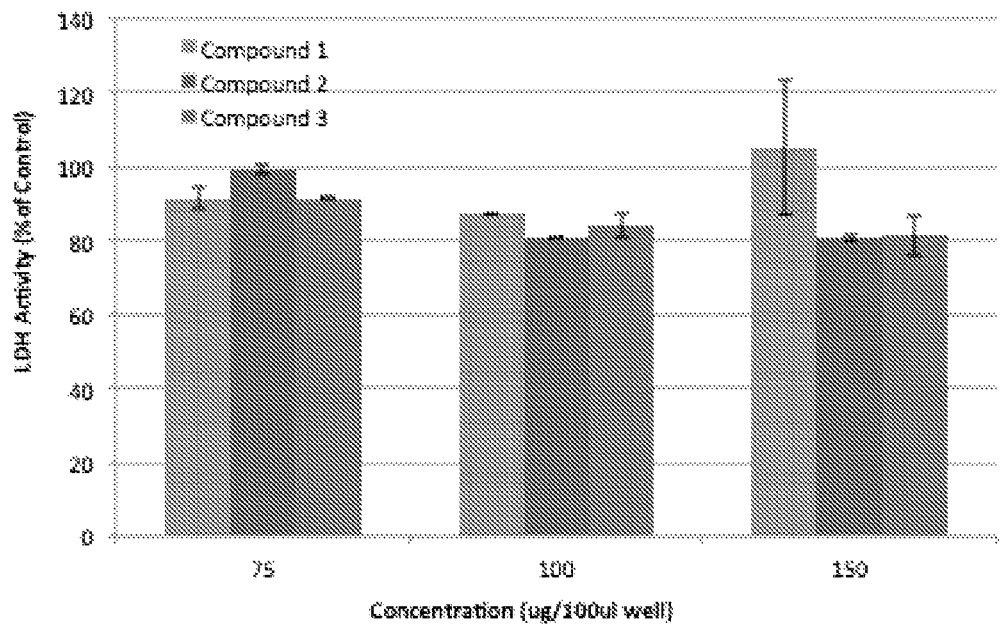
FIG. 12 shows LDH activity of MCF-7, human breast cancer cells after treatment with compounds of the present invention.
Figure 13:
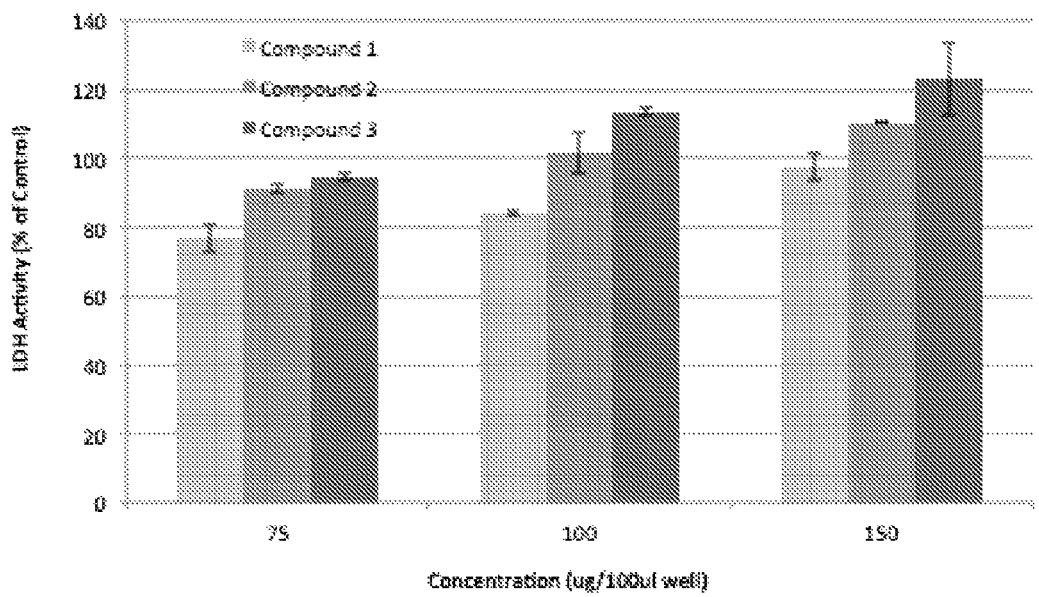
FIG. 13 shows LDH activity of T47-D, human breast cancer cells after treatment with compounds of the present invention.

The results are shown in FIGS. 12-13.

b) subjecting the lignin-containing starting raw material of step (a) to alkaline treatment by adding sodium hydroxide to obtain a solution of sodium salts of benzene polycarboxylic acids, c) subjecting the solution of sodium salts of benzene polycarboxylic acids of step (b) to acid density gradient treatment to obtain crude polymer of benzene polycarboxylic acids, and d) purifying the crude polymer of benzene polycarboxylic acids of step (c) by removing low-molecular impurities to obtain the purified water-soluble polymer compound of benzene polycarboxylic acids.

5. The process according to claim 4,
wherein the alkaline treatment of step (b) is performed by reacting an alkaline suspension of lignin-containing starting raw material of step (a) with oxygen at a pH of 13±0.5 and a pressure of 2.2±0.3 MPa and/or,
wherein the acid density gradient treatment of step (c) is performed by subjecting the solution of sodium salts of benzene polycarboxylic acids of step (b) to treatment with a mineral acid to obtain a pH of 1-2 and subsequently to action of centrifugal force and/or,
wherein the purification in step (d) is performed by subjecting the crude polymer of benzene polycarboxylic acids of step (c) to one or more purifying processes selected from extraction, flotation, distilllation, filtration, precipitation, centrifugation, decantation and dialysis.

6. A cosmetic composition comprising the compound according to claim 1 or, a nutraceutical composition comprising the compound according to claim 1, wherein said composition optionally may further comprise nutrients.

7. A composite substance comprising a water-soluble polymer compound of benzene polycarboxylic acids according to claim 1 and a metal cation.

8. The composite substance according to claim 7, wherein the metal cation is selected from the group of 2s-5s or 3d-5d elements.

9. A pharmaceutical composition comprising the composite substance according to claim 7, wherein said pharmaceutical composition further comprises an anti-cancer agent.

10. A composite substance comprising the water-soluble polymer compound of benzene polycarboxylic acids according to claim 1 and a platinum (II) square planar coordination compound, wherein the polymer compound of benzene polycarboxylic acids encapsulates or forms a complex with said platinum (II) compound.

11. The composite substance according to claim 10, wherein the composite substance has a molecular formula of $(C_3H_2O)_{x1}(C_2H_2O)_{x2}(CH_2)_{x3}(Pt(NH_3)_2)_{x4}$, where x1, x2, x3 and x4 are the coefficients representing any natural, positive, full or fractional number.

12. The composite substance according to claim 10, wherein the platinum compound is either encapsulated by or forms a complex with one of the following structures of the polymer compound of benzene polycarboxylic acids

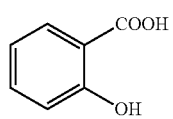
(a)

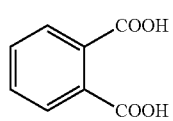
(b)

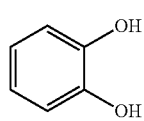
(c)

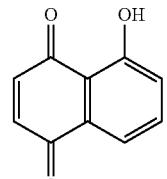
(d)

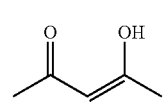
(e)

where the structures a, b, c and d represent moieties of aromatic components selected from 3-benzyloxy-4,5-dihydroxy-benzoic acid methyl ester, 5-(furan-2-carbonyloxy)-2-methyl-benzofuran-3-carboxylic acid methyl ester, 2,6-dimethyl-benzo(1,2-b,4,5-b')difuran-3,7-dicarboxylic acid dimethyl ester, 5-(furan-2-carbonyloxy)-2-methyl-benzofuran-3-carboxylic acid ethyl ester, rhamnetin, methyl ((4-methyl-6-oxo-6h-benzo(c)chromen-3-yl)oxy)acetate hydrate, bis(2-(methoxycarbonyl)phenyl) carbonate, sulochrin, 2,6-diacetyl-7,9-dihydroxy-8,9b-dimethyldibenzofuran-1,3(2H,9bH)-dione, O-acetylsalicylic anhydride, 4-ho-3-((6-ho-benzo(1,3)dioxol-5-yl)-(3-methoxy-phenyl)-methyl)-5h-furan-2-one, 2,3-bis-benzoyloxy-succinic acid, methyl 5-hydroxy-7,8-dimethoxy-1,3-dioxo-1,3,10,11-tetrahydrobenzo[5,6]cycloocta[1,2-c]furan-4-carboxylate, (1-methoxycarbonylmethoxy-6-oxo-6h-benzo(c)chromen-3-yloxy)-acetic acid methyl ester, atranorin and phenylpropanoid-substituted epicatechins and structure e represents a moiety of the acids, wherein said acid is a saturated aliphatic hydroxycarboxylic acids selected from hydroxyhexadecanoic acid, hydroxyoctadecanoic acid, dihydroxyoctadecanoic acid, hydroxyeicosanoic acid, trihydroxyoctadecanoic acid, hydroxydocosanoic acid, hydroxytetracosanoic acid and hydroxypentacosanoic acid; or a monounsaturated aliphatic carboxylic acid selected from hexadecenoic acid, heptadecenoic acid, octadecenoic acid and eicosenoic acid or a monounsaturated aliphatic hydroxycarboxylic acids selected from hydroxyoctadecenoic acid, dihydroxyoctadecenoic acid, dihydroxyeicosenoic acid, tetrahydroxyoctadecenoic acid and dihydroxydocosenoic acid.

13. A process for preparing the composite substance according to claim 10 comprising the steps of:
a1) providing a lignin-containing starting raw material, which is produced from conifer trees and has a pH from 5.5 to 7, a moisture content from 50 to 70% and comprises no more than 32% of polysaccharides, no less than 66% of lignin and no more than 2% of water-soluble compounds,
1) subjecting the lignin-containing starting raw material of step a1 to alkaline treatment by adding sodium hydroxide to obtain a solution of sodium salts of benzene polycarboxylic acids,
c1) subjecting solution of sodium salts of benzene polycarboxylic acids of step b1 to acid density gradient treatment to obtain a crude polymer of benzene polycarboxylic acids,
d1) purifying the crude polymer of benzene polycarboxylic acids of step c1 to obtain a purified polymer of benzene polycarboxylic acids,
e1) reacting the purified polymer of benzene polycarboxylic acids obtained in step d1 with a platinum (II) square planar coordination compound to obtain a reaction mixture, f1) thermostating the reaction mixture of step e1 to obtain crude composite substance, and g1) purifying the crude composite substance of step f1 to obtain the composite substance.

14. The process according to claim 13,
wherein the alkaline treatment of step b1 is performed by reacting an alkaline suspension of lignin-containing material of step a1 with oxygen at a pH of 13±0.5 and a pressure of 2.2±0.3 MPa, and/or,
wherein the acid density gradient treatment of step c1 is performed by subjecting the solution of sodium salts of benzene polycarboxylic acids of step b1 to treatment with a mineral acid to obtain a pH of 1-2 and subsequently to action of centrifugal force, and/or,
wherein the purifying in step d1 is performed by subjecting the crude polymer of benzene polycarboxylic acids of step c1 to one or more purifying processes selected from extraction, flotation, distillation, filtration, precipitation, centrifugation, decantation and dialysis.

15. The process according to claim 13, wherein the square planar coordination platinum compound is cis-diammineplatinum (II) dichloride or potassium tetrachloroplatinate or the mixture thereof.

16. A method for treatment of cancer in a mammal, said method comprising administering the composite substance according to claim 10 to the mammal in need thereof.

17. A composite substance comprising the water-soluble polymer compound of benzene polycarboxylic acids according to claim 1 and a molybdenum compound in the form of a molybdenum acids salt.

18. The composite substance according to claim 17, wherein the composite substance has a molecular formula of $(C_3H_2O)_{x1}(C_2H_2O)_{x2}(CH_2)_{x3}(MoO_3)_{x4}(H_2O)_{x5}(NH_4)_{x6}$, where $x_1$, $x_2$, $x_3$, $x_4$, $x_5$ and $x_6$ are the coefficients representing any natural, positive, full or fractional number.

19. The composite substance according to claim 17, wherein the molybdenum compound is either encapsulated by or forms complex with one of the following structures of the polymer compound of benzene polycarboxylic acids

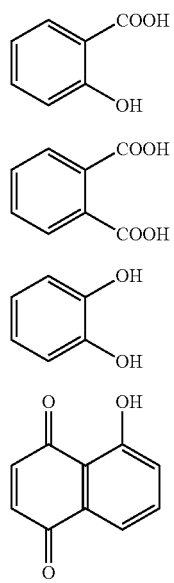

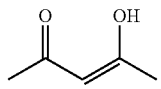

where the structures a, b, c and d represent moieties of aromatic components selected from 3-benzyloxy-4,5-dihydroxy-benzoic acid methyl ester, 5-(furan-2-carbonyloxy)-2-methyl-benzofuran-3-carboxylic acid methyl ester, 2,6-dimethyl-benzo(1,2-b,4,5-b')difuran-3,7-dicarboxylic acid dimethyl ester, 5-(furan-2-carbonyloxy)-2-methyl-benzofuran-3-carboxylic acid ethyl ester, rhamnetin, methyl ((4-methyl-6-oxo-6h -benzo(c)chromen-3-yl)oxy)acetate hydrate, bis(2-(methoxycarbonyl)phenyl) carbonate, sulochrin, 2,6-diacetyl-7,9-dihydroxy-8,9b-dimethyldibenzofuran-1,3(2H,9bH)-dione, O -acetylsalicylic anhydride, 4-ho-3-((6-ho-benzo(1,3)dioxol-5-yl)-(3-methoxy-phenyl) -methyl)-5h-furan-2-one, 2,3-bis-benzoyloxy-succinic acid, methyl 5-hydroxy-7,8-dimethoxy-1,3-dioxo-1,3,10,11-tetrahydrobenzo[5,6]cycloocta[1,2-c]furan-4-carboxylate, (1-methoxycarbonylmethoxy-6-oxo-6h-benzo(c)chromen-3-yloxy)-acetic acid methyl ester, atranorin and phenylpropanoid-substituted epicatechins and structure e represents a moiety of the acids wherein said acid is a saturated aliphatic hydroxycarboxylic acids selected from hydroxyhexadecanoic acid, hydroxyoctadecanoic acid, dihydroxyoctadecanoic acid, hydroxyeicosanoic acid, trihydroxyoctadecanoic acid, hydroxydocosanoic acid, hydroxytetracosanoic acid and hydroxypentacosanoic acid; or a monounsaturated aliphatic carboxylic acid selected from hexadecenoic acid, heptadecenoic acid, octadecenoic acid and eicosenoic acid or a monounsaturated aliphatic hydroxycarboxylic acids selected from hydroxyoctadecenoic acid, dihydroxyoctadecenoic acid, dihydroxyeicosenoic acid, tetrahydroxyoctadecenoic acid and dihydroxydocosenoic acid.

20. A process for preparing a composite substance, comprising a water-soluble polymer compound of benzene polycarboxylic acids according to claim 1 and a molybdenum compound, the process comprising:

a2) providing a lignin-containing starting raw material, which is produced from conifer trees and has a pH from 5.5 to 7, a moisture content from 50 to 70% and comprises no more than 32% of polysaccharides, no less than 66% of lignin and no more than 2% of water-soluble compounds, b2) subjecting the lignin-containing starting raw material of step a2 to alkaline treatment by adding sodium hydroxide to obtain a solution of sodium salts of benzene polycarboxylic acids, c2) subjecting solution of sodium salts of benzene polycarboxylic acids of step b2 to acid density gradient treatment to obtain crude polymer of benzene polycarboxylic acids, d2) purifying the crude polymer of benzene polycarboxylic acids of step c2 to obtain a purified polymer of benzene polycarboxylic acids, e2) reacting the purified polymer of benzene polycarboxylic acids obtained in step d2 with a molybdenum compound to obtain a reaction mixture, f2) thermostating the reaction mixture of step e2 to obtain crude composite substance, g2) purifying the crude composite substance of step f2 to obtain the composite substance.

21. The process according to claim 20,
wherein the alkaline treatment of step b2 is performed by reacting an alkaline suspension of lignin-containing material of step a2 with oxygen at a pH of 13±0.5 and a pressure of 2.2±0.3 MPa; and/or
wherein the acid density gradient treatment of step c2 is performed by subjecting the solution of sodium salts of benzene polycarboxylic acids of step b2 to treatment with a mineral acid and subsequently to action of centrifugal force; and/or
wherein the purifying in step d2 is performed by subjecting the crude polymer of benzene polycarboxylic acids of step c2 to one or more purifying processes selected from extraction, flotation, distillation, filtration, precipitation, centrifugation, decantation and dialysis.

22. The process according to claim 20, wherein the molybdenum compound is a molybdenum acids salt selected from ammonium molybdate, ammonium molybdate tetrahydrate, potassium molybdate, sodium molybdate, sodium molybdate dihydrate or a mixture thereof.

23. A method for treatment of cancer in a mammal, said method comprising administering the composite substance according to claim 17 to the mammal in need thereof.

24. A method for treatment or palliative care of a mammal suffering from cancer, comprising administering a composite substance according to claim 17 to the mammal in need thereof.

25. A method for reducing/minimising side effects resulting from conventional radiotherapy or chemotherapy in a mammal, comprising administering the composite substance according to claim 17 to a mammal in need thereof.

* * * * *

UNITED STATES PATENT AND TRADEMARK OFFICE
CERTIFICATE OF CORRECTION

PATENT NO. : 9,644,074 B2
APPLICATION NO. : 14/389063
DATED : May 9, 2017
INVENTOR(S) : Valery Pavlovich Shipov, Evgeny Sergeevich Pigarev and Elena I. Fedoros It is certified that error appears in the above-identified patent and that said Letters Patent is hereby corrected as shown below:

On the Title Page

Item (73) Assignee:
Please delete: "RINNOVATION APS, Copenhagen (DK)"
And insert: -- RDINNOVATION APS, Copenhagen (DK) --.

Signed and Sealed this
Twenty-fifth Day of July, 2017

Joseph Matal
*Performing the Functions and Duties of the*
*Under Secretary of Commerce for Intellectual Property and*
*Director of the United States Patent and Trademark Office*